(12) United States Patent
Deno et al.

(10) Patent No.: US 12,350,055 B2
(45) Date of Patent: Jul. 8, 2025

(54) ELECTROPHYSIOLOGY LABORATORY SYSTEM FOR USE WITH MAGNETIC RESONANCE IMAGING SYSTEMS

(71) Applicant: St. Jude Medical, Atrial Fibrillation Division, Inc., St. Paul, MN (US)

(72) Inventors: D. Curtis Deno, Andover, MN (US); Jeffrey A. Schweitzer, St. Paul, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1243 days.

(21) Appl. No.: 16/798,243

(22) Filed: Feb. 21, 2020

(65) Prior Publication Data

US 2020/0187824 A1    Jun. 18, 2020

Related U.S. Application Data

(62) Division of application No. 14/396,008, filed as application No. PCT/US2013/031921 on Mar. 15, 2013, now Pat. No. 10,610,127.

(Continued)

(51) Int. Cl.
*A61B 18/18*        (2006.01)
*A61B 5/00*         (2006.01)
(Continued)

(52) U.S. Cl.
CPC .......... *A61B 5/283* (2021.01); *A61B 5/02055* (2013.01); *A61B 5/055* (2013.01);
(Continued)

(58) Field of Classification Search
CPC ........ A61N 1/086; A61N 1/05; A61N 1/3718; A61N 1/37; A61N 1/08; A61B 18/1492;
(Continued)

(56) References Cited

U.S. PATENT DOCUMENTS 5,357,956 A    10/1994  Nardella
6,233,476 B1    5/2001  Strommer
(Continued)

FOREIGN PATENT DOCUMENTS

WO    2008032249    3/2008

*Primary Examiner* — Joseph A Stoklosa
*Assistant Examiner* — Brian M Antiskay
(74) *Attorney, Agent, or Firm* — Armstrong Teasdale LLP

(57) ABSTRACT

An electrophysiological laboratory system comprises a subsystem configured to perform diagnostic and/or therapeutic functions, a medical device, and an interface module disposed therebetween. The medical device comprises a shaft having proximal and distal portions, high- and low-impedance electrical pathways disposed within the shaft, and an electrode disposed at the distal portion of the shaft and electrically coupled to one or both of the high- and low-impedance electrical pathways. The electrode is configured to perform diagnostic and/or therapy delivery functions. The interface module comprises a high-impedance channel configured to couple the high-impedance pathway of the medical device to the subsystem, and to attenuate magnetic resonance RF and gradient field pulses generated by the MRI system. The interface module further comprises a low-impedance channel configured to couple the low-impedance pathway of the medical device to the subsystem.

20 Claims, 6 Drawing Sheets

Related U.S. Application Data

(60) Provisional application No. 61/636,971, filed on Apr. 23, 2012.

(51) Int. Cl.

| | | |
|---|---|---|
| *A61B 5/0205* | (2006.01) | |
| *A61B 5/055* | (2006.01) | |
| *A61B 5/06* | (2006.01) | |
| *A61B 5/283* | (2021.01) | |
| *A61B 5/287* | (2021.01) | |
| *A61B 18/14* | (2006.01) | |
| *A61N 1/05* | (2006.01) | |
| *A61N 1/36* | (2006.01) | |
| *G01R 33/28* | (2006.01) | |
| *A61B 18/00* | (2006.01) | |
| *A61B 34/20* | (2016.01) | |
| *A61B 90/00* | (2016.01) | |
| *G01R 33/36* | (2006.01) | |

(52) U.S. Cl.
CPC .............. *A61B 5/063* (2013.01); *A61B 5/287* (2021.01); *A61B 5/6852* (2013.01); *A61B 5/7203* (2013.01); *A61B 18/1492* (2013.01); *A61N 1/05* (2013.01); *A61N 1/36* (2013.01); *G01R 33/285* (2013.01); *A61B 2018/00577* (2013.01); *A61B 2034/2051* (2016.02); *A61B 2090/374* (2016.02); *A61B 2562/18* (2013.01); *G01R 33/3685* (2013.01)

(58) Field of Classification Search
CPC .... A61B 2090/374; A61B 2018/00839; A61B 5/055; A61B 5/283; A61B 5/30; A61B 2034/2051; A61B 2018/00875; A61B 2018/1467; A61B 2562/18; A61B 2562/222; A61B 18/1206; A61B 2562/182; A61B 5/282; A61B 8/445

USPC ................ 600/372–373, 377, 407, 410–412; 607/115

See application file for complete search history.

(56) References Cited

U.S. PATENT DOCUMENTS

| | | |
|---|---|---|
| 6,498,944 B1 | 12/2002 | Ben-Haim |
| 6,690,963 B2 | 2/2004 | Ben-Haim |
| 6,788,967 B2 | 9/2004 | Ben-Haim |
| 7,197,354 B2 | 3/2007 | Sobe |
| 7,263,397 B2 | 8/2007 | Hauck |
| 7,386,339 B2 | 8/2008 | Strommer |
| 7,734,354 B1 | 6/2010 | Cox |
| 8,805,540 B2 | 6/2014 | Lloyd |
| 2004/0236202 A1 | 11/2004 | Burton |
| 2006/0030774 A1 | 2/2006 | Gray |
| 2007/0198007 A1 | 8/2007 | Govari |
| 2008/0097231 A1 | 4/2008 | Balda et al. |
| 2009/0149909 A1 | 6/2009 | Ameri |
| 2009/0163904 A1* | 6/2009 | Miller .................... A61B 5/053 606/33 |
| 2010/0023000 A1 | 1/2010 | Stevenson |
| 2010/0106154 A1* | 4/2010 | Harlev .................. A61B 34/20 600/407 |
| 2011/0046700 A1* | 2/2011 | McDonald ............... A61N 1/05 607/63 |
| 2011/0125077 A1 | 5/2011 | Denison |
| 2011/0160558 A1* | 6/2011 | Rassatt .................. A61B 90/94 600/377 |
| 2012/0065536 A1* | 3/2012 | Causevic ................. A61B 5/30 600/544 |
| 2012/0253340 A1* | 10/2012 | Stevenson ............ H03H 7/0123 607/116 |
| 2013/0072772 A1 | 3/2013 | Fandrey |
| 2014/0024909 A1 | 1/2014 | Vij et al. |

* cited by examiner

ELECTROPHYSIOLOGY LABORATORY SYSTEM FOR USE WITH MAGNETIC RESONANCE IMAGING SYSTEMS

CROSS-REFERENCE TO RELATED APPLICATIONS

This application is a divisional of U.S. application Ser. No. 14/396,008, filed 21 Oct. 2014, which is the National Stage of International Application No. PCT/US2013/031921, filed 23 Apr. 2012, which claims the benefit of U.S. provisional application No. 61/636,971, filed 23 Apr. 2012, all of which are incorporated by reference in their entirety as though fully set forth herein.

BACKGROUND a. Technical Field

This disclosure relates to an electrophysiology laboratory (EP lab) system. More particularly, this disclosure relates to an EP lab system configured for use in conjunction with a magnetic resonance imaging (MRI) system, wherein some or all of the constituent components of the EP lab system are MRI-compatible, thereby rendering the EP lab system MRI-compatible.

b. Background Art

It is well known that various types of imaging systems may be used as part of, or in conjunction with, EP lab systems to provide visualization of anatomic structures during various diagnostic and/or therapeutic procedures. Conventional imaging or visualization techniques that have been used for this purpose include, for example, fluoroscopic imaging, ultrasound imaging, and three-dimensional visualization or modeling and mapping techniques, among others.

The use of conventional techniques such as those identified above have not been without their disadvantages, however. For example, fluoroscopy-based techniques require the use of radiation, which thereby necessarily results in radiation exposure to the patient. Further, while conventional techniques provide important visualization capabilities, they may be undesirably limited in the amount of detail relating to, for example, assessment of scar or ablation lesion formation and tissue characterization, as well as in the three-dimensional visualization required for certain cardiac applications, including, for example, transseptal access.

One imaging or visualization technique that may overcome at least some of the drawbacks of those conventional techniques described above is magnetic resonance imaging (MRI). MRI is desirable for its radiation-free volumetric images that can be segmented or used "as is" for cardiac anatomy and tissue characterization, for example. It has been observed that MRI provides desirable imaging or visualization of tissue changes during ablation lesion formation and also provides good mechanical functional assessments. Unfortunately, MRI also provides challenges with respect to its use with EP lab systems, and the constituent components thereof, in particular.

For example, MRI involves three electromagnetic components that place constraints on materials used in medical devices (e.g., catheters) and other EP lab system components, as well as in the way electrical signals are processed. More particularly, MRI involves a large static magnetic field that places restrictions on the use of ferromagnetic materials commonly used in medical devices such as catheters. MRI also involves magnetic resonance radio frequency pulses having a frequency on the order of 63.9 MHz for a 1.5 Tesla MRI system. These pulses may cause interference in electrical signals transmitted or communicated within the EP lab system, and may also induce currents that may be sufficient to heat conductors and cause damage to components of the EP lab system and adjacent tissue. Further, MRI involves magnetic resonance gradient field pulses that are used to encode spatial location in nuclear resonant frequencies. These pulses may induce signal artifacts that resemble cardiac electrograms and interfere with electrical signals transmitted or communicated in the EP lab system, or other sensors/components of the EP lab system.

Accordingly, the inventors herein have recognized a need for an EP lab system that is configured for use with an MRI system and that will minimize and/or eliminate one or more of the deficiencies in conventional systems, as well as the difficulties or challenges with respect to the use of MRI in conjunction with EP lab systems.

BRIEF SUMMARY

In various embodiments, the present disclosure is generally directed to electrophysiology laboratory (EP lab) systems, and the constituent components thereof, configured for use with magnetic resonance imaging (MRI) systems.

In accordance with one aspect of the present teachings, an MRI-compatible medical device is provided. The medical device comprises an elongate shaft having a proximal portion and a distal portion, and at least one electrode disposed at the distal portion of the shaft configured to perform diagnostic and/or therapy delivery functions. The medical device may further comprise a high-impedance electrical pathway disposed within the shaft and extending from the distal portion to the proximal portion thereof, and a low-impedance electrical pathway also disposed within the shaft and extending from the distal portion to the proximal portion thereof. The electrode may be electrically coupled to one or both of the high-impedance electrical pathway and the low-impedance electrical pathway.

In accordance with another aspect of the present teachings, an interface module of an EP lab system configured for use with an MRI system is provided. The interface module may comprise a high-impedance channel and a low-impedance channel. The high-impedance channel comprises an electrical pathway configured to electrically couple a high-impedance electrical pathway of a medical device with a diagnostic and/or therapeutic subsystem of the EP lab system. The electrical pathway is further configured to attenuate magnetic resonance radio frequency and gradient field pulses generated by the MRI system. The low-impedance channel comprises a plurality of electrical pathways configured to electrically couple a low-impedance electrical pathway of the medical device to a diagnostic and/or therapeutic subsystem of the EP lab system.

In accordance with yet another aspect, an EP lab system configured for use with an MRI system is provided. The EP lab system comprises a subsystem configured to perform diagnostic and/or therapeutic functions, an MRI-compatible medical device, and an interface module disposed between the medical device and the subsystem.

In an exemplary embodiment, the medical device comprises an elongate shaft having a proximal portion and a distal portion, a high-impedance electrical pathway and a low-impedance electrical pathway each disposed within the shaft and extending from the distal portion to the proximal portion thereof, and at least one electrode disposed at the distal portion of the shaft configured to perform diagnostic and/or therapy delivery functions. The electrode may be electrically coupled to one or both of the high-impedance and low-impedance electrical pathways.

In an exemplary embodiment, the interface module comprises a high-impedance channel and a low-impedance channel. The high-impedance channel comprises an electrical pathway configured to electrically couple the high-impedance electrical pathway of the medical device to the subsystem. The electrical pathway is further configured to attenuate magnetic resonance radio frequency and gradient field pulses generated by the MRI system. The low-impedance channel comprises a plurality of electrical pathways configured to electrically couple the low-impedance electrical pathway of the medical device to the subsystem.

The foregoing and other aspects, features, details, utilities, and advantages of the present disclosure will be apparent from reading the following description and claims, and from reviewing the accompanying drawings.

DETAILED DESCRIPTION

Various embodiments are described herein relating to various apparatus, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," "an embodiment," "an exemplary embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," "in an exemplary embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Figure 1:
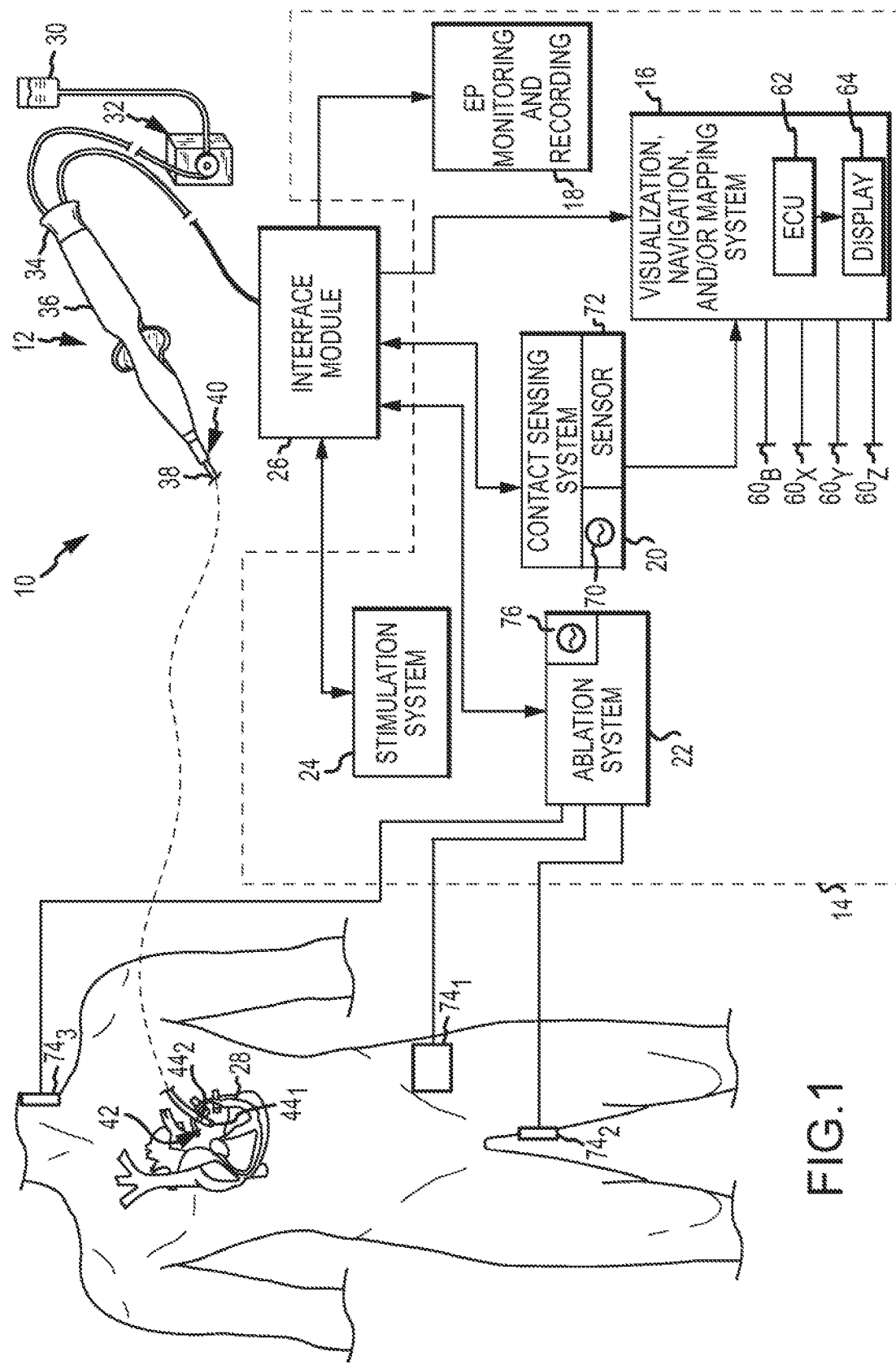
FIG. 1 is a diagrammatic view of an exemplary electrophysiology laboratory (EP lab) system in accordance with the present teachings.

Referring now to the drawings wherein like reference numerals are used to identify identical or similar components in the various views, FIG. 1 illustrates one exemplary embodiment of an electrophysiology laboratory system 10 (EP lab system 10) for use with a magnetic resonance imaging (MRI) system. The EP lab system 10 comprises a number of components and/or subsystems. For example, in an exemplary embodiment, the EP lab system 10 comprises one or more medical devices 12 (e.g., a catheter 12) and one or more diagnostic and/or therapeutic subsystems 14, such as, for example and without limitation, a visualization, navigation, and/or mapping system 16, an EP monitoring and recording system 18 (e.g., for monitoring and/or recording electrocardiograms (EGM), cardiac signals, etc.), a tissue contact sensing system 20, an ablation system 22, and a cardiac stimulation system 24 (i.e., EP stimulator 24). The system 10 further comprises an interface module 26 disposed between and electrically coupled to the medical device 12 and one or more of the diagnostic and/or therapeutic subsystem(s) 14. For purposes of clarity and illustration, the description set forth below will be with respect to an EP lab system used for cardiac-related applications only. It should be understood, however, that the present disclosure may be implemented and find use in connection with any number of other anatomical-related applications that include the use of an MRI system. Accordingly, the present disclosure is not intended to be limited to cardiac-related applications.

As illustrated in FIG. 1, the catheter 12 is provided for examination, diagnosis, and/or treatment of internal body tissues such as cardiac tissue 28. In an exemplary embodiment, the catheter 12 comprises an ablation catheter and, more particularly, an irrigated radio-frequency (RF) ablation catheter. It should be understood, however, that the catheter 12 is not limited to an irrigated catheter or an RF ablation catheter. Rather, in other embodiments, the catheter 12 may comprise a non-irrigated and/or other types of ablation catheters (e.g., cryoablation, ultrasound, etc.). In still further embodiments, the catheter 12 may not comprise an ablation catheter at all, rather it may comprise a catheter configured to perform other diagnostic and/or therapeutic functions. In the exemplary embodiment wherein the catheter 12 is an irrigated RF catheter, however, the catheter 12 is connected to a fluid source 30 providing a biocompatible fluid such as saline through a pump 32 (which may comprise, for example, a fixed rate roller pump or variable volume syringe pump with a gravity feed supply from the fluid source 30, as shown) for irrigation.

In an exemplary embodiment, the catheter 12 is electrically coupled to one or more diagnostic and/or therapeutic subsystems 14 of the EP lab system 10, such as, for example, the ablation system 22 to allow for the delivery of RF energy. The catheter 12 may include a cable connector or interface 34, a handle 36, a shaft 38 having a proximal portion 40 and a distal portion 42, and one or more sensors and/or electrodes 44 mounted in or on the shaft 38 at or near the distal portion 42 thereof that are configured to perform, as will be described below, one or more diagnostic and/or therapy delivery functions. In an exemplary embodiment, the catheter 12 includes a single electrode 44. In other exemplary embodiments, however, the catheter 12 may comprise a plurality of electrodes 44 (i.e., electrodes $44_1$, $44_2$, . . . , $44_N$). In either instance, the electrode(s) 44 may be provided for a variety of diagnostic and/or therapeutic purposes including, for example and without limitation, electrophysiological studies, catheter identification and location, stimulation or pacing, cardiac mapping, and ablation. In addition to the electrode(s) 44, the catheter 12 may further include other sensors or components, such as, for example and without limitation, a temperature sensor (e.g., thermistor or thermocouple), ablation elements (e.g., high intensity focused ultrasound ablation elements, etc.), and corresponding conductors or leads.

The connector 34 provides a mechanical, fluid, and electrical connection(s) between the catheter 12 and other components of the EP lab system 10, such as, for example and without limitation, the pump 32 of the ablation system 22 and the interface module 26. The connector 34 is conventional in the art and is disposed at the proximal portion 40 of the catheter 12.

The handle 36 provides a location for the clinician to hold the catheter 12 and may further provide means for steering or guiding the shaft 38 within the body of the patient. For example, the handle 36 may include means to change the length of a pull wire extending through the shaft 38 to the distal portion 42 thereof to steer the shaft 38. The handle 36 is also conventional in the art and it will be understood that the construction of the handle 36 may vary. In another exemplary embodiment, the control of the catheter 12 may be at least partially automated. Accordingly, rather than a clinician manipulating a handle to steer or guide the catheter 12, and the shaft 38 thereof, in particular, a robot or another automated control/guidance system may be used to manipulate the catheter 12.

Figure 2A:
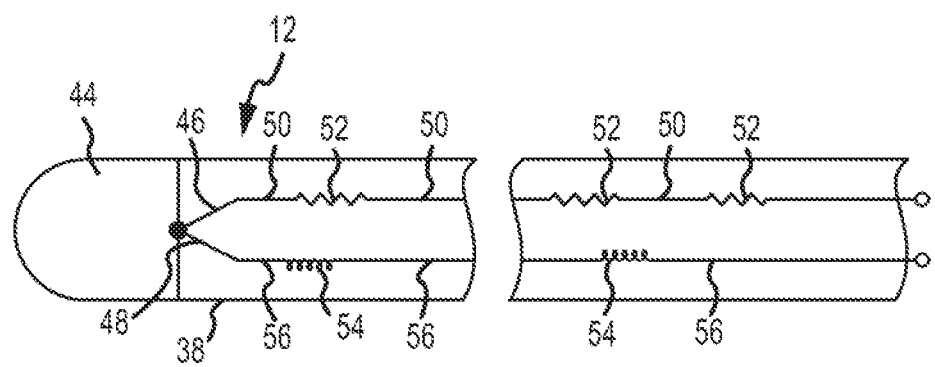
FIG. 2A is a diagrammatic view of a portion of an exemplary medical device of the EP lab illustrated in FIG. 1.
Figure 2B:
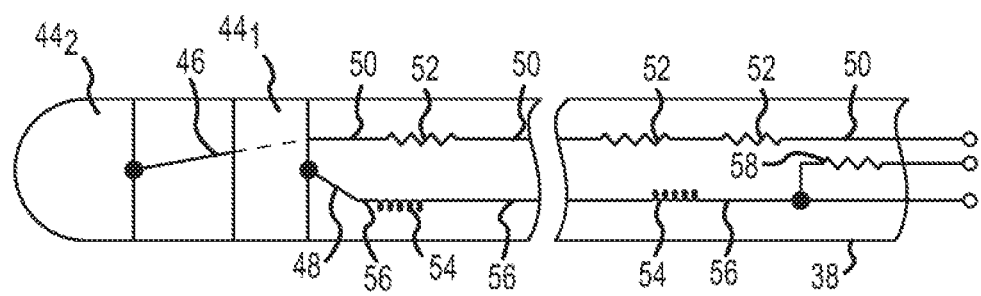
FIG. 2B is diagrammatic view of a portion of another exemplary medical device of the EP lab system illustrated in FIG. 1.

In any event, and with reference to FIGS. 1-2B, the shaft 38 is an elongate, tubular, flexible member configured for movement within the body of a patient. The shaft 38 supports, for example and without limitation, the electrode(s) 44 and/or other components of the catheter 12, and may also permit transport, delivery, and/or removal of fluids (including irrigation fluids, cryogenic ablation fluids, and bodily fluids), medicines, and/or surgical tools or instruments. To that end, the shaft 38 may be made from conventional materials such as polyurethane, and defines one or more lumens configured to house and/or transport components of the catheter 12, fluids, or surgical tools, for example. The shaft 38 may be introduced into a blood vessel or other structure within a patient's body and then steered or guided through the patient's body to a desired location.

With reference to FIGS. 2A and 2B, in an exemplary embodiment, the catheter 12 further comprises a plurality of electrical pathways disposed within the shaft 38 (e.g., within one or more lumens therein, for example) that are configured to electrically couple the electrode(s) 44 or other components of the catheter 12 with other components of the EP lab system 10 (e.g., one or more subsystems 14 or the interface module 26). Because the EP lab system 10 and therefore the catheter 12 is intended to be used with an MRI system, the electrical pathways of the catheter 12 must be configured to allow for the transmission of electrical signals between the electrodes 44 and other components of the EP lab system 10 without interference or distortion, and also to prevent damage to the catheter 12 or surrounding tissue. More particularly, MRI involves three electromagnetic components that place constraints on catheter design and signal processing. A first component is the large magnetic static field (e.g., 1.5 Tesla) that is generated by the MRI system. This particular component imposes restrictions on the use of ferromagnetic materials in catheters and other components of the EP lab system 10. A second component is the magnetic resonance RF pulses generated by the MRI system to excite hydrogen nuclei. These pulses may be on the order of 63.9 MHz for a 1.5 T system, and may interfere with signals transmitted along the electrical pathways of the catheter 12, and also induce currents therein that are sufficient to heat the electrodes 44 and conductors of the electrical pathways of the catheter 12 to such a degree that the catheter 12, and/or tissue in close proximity thereto, may be damaged. Finally, a third component is the magnetic resonance gradient field pulses generated by the MRI system to encode spatial location in nuclear resonant frequencies. These gradient pulses may induce large signal artifacts that resemble, for example, EGMs, and may interfere with electrical signals communicated between the electrodes 44 or other sensors/components of the catheter 12 and other components of the EP lab system 10. Accordingly, certain measures must be taken to account for these inherent characteristics of MRI systems and their consequences to render the catheter 12 MRI-compatible.

As such, and with continued reference to FIGS. 2A and 2B, in an exemplary embodiment, the catheter 12 comprises one or more high-impedance electrical pathways 46 over which certain electrical signals can be transmitted or communicated from one or more electrodes 44 to one or more subsystems 14 (either directly or, as will be described below, via the interface module 26). High-impedance electrical pathways 46 are suitable to both allow for the transmission of certain types of electrical signals (e.g., those used in determining the position and orientation of the electrode(s) 44 and EGM signals, for example), and also to prevent the inducement of RF currents therein by the RF magnetic resonance pulses described above.

In an exemplary embodiment, the catheter 12 may further comprise one or more electrical pathways 48 that at relatively high frequencies (e.g., 63.9 MHz) comprise high-impedance pathways so as to avoid, for example, heating or the introduction of magnetic resonance imaging artifacts, but that at relatively lower frequencies (e.g., 0-500 kHz or greater) comprise low-impedance electrical pathways (hereinafter referred to as "low-impedance electrical pathways 48") to allow for the transmission or communication of certain electrical signals associated with, for example, pacing and delivery of ablative energy. More particularly, the low-impedance electrical pathways 48 provide a pathway over which certain electrical signals may be transmitted or communicated from one or more electrodes 44 or other sensors/components of the catheter 12 to one or more subsystems 14 (either directly or, as will be described below, via the interface module 26), and over which electrical energy (e.g., ablative energy, pacing or stimulation pulses, activation signals, etc.) may be transmitted or communicated from one or more subsystems 14 to one or more electrodes 44. As will be described more fully below, when combined with one or more inductive elements, the low-impedance electrical pathways 48 are suitable to allow for the transmission of certain types of electrical signals (e.g., tissue contact sensing signals, signals generated by thermistors or thermocouples, etc.), and to prevent the inducement of RF currents therein by the RF magnetic resonance pulses described above.

As illustrated in FIG. 2A, in an exemplary embodiment, the catheter 12 comprises a single electrode 44 that is configured to perform both a diagnostic function (e.g., sensing) and a therapy or electrical energy delivery function. In such an embodiment, both the high- and low-impedance electrical pathways 46, 48 are electrically coupled to the electrode 44.

In another exemplary embodiment such as that illustrated in FIG. 2B, the catheter 12 comprises a pair of electrodes 44 (i.e., electrodes $44_1$, $44_2$). In such an embodiment, one of the electrodes 44, electrode $44_2$, for example, may be configured to perform a diagnostic function, such as, for example and without limitation, position sensing, EGM sensing, etc. In an exemplary embodiment, the electrical signals generated or sensed by the electrode $44_2$ are of the type that, when in an MRI environment, can be transmitted or communicated over a high-impedance electrical pathway between the electrode $44_2$ and one or more subsystems 14 of the EP lab system 10. Accordingly, in an exemplary embodiment, the electrode $44_2$ is electrically coupled to the high-impedance electrical pathway 46 of the catheter 12.

Conversely, one or more of the other electrodes 44, electrode $44_1$, for example, may be configured to perform a therapy delivery function and/or a sensing function (e.g., delivery of ablative energy, delivery of stimulation or pacing pulses, delivery of activation signals/energy, impedance sensing, temperature sensing, etc.). In an exemplary embodiment, the electrical signals generated or sensed by, or delivered to, the electrode $44_1$ are of a type that, when in an MRI environment, can or must be transmitted or communicated over a low-impedance electrical pathway between the electrode $44_1$ and one or more subsystems 14 of the EP lab system 10. Accordingly, in an exemplary embodiment, the electrode $44_1$ is electrically coupled to the low-impedance electrical pathway 48 of the catheter 12.

For purposes of illustration, the description below will be limited to an embodiment wherein the catheter 12 comprises a pair of electrodes $44_1$, $44_2$ and one of each of a high-impedance electrical pathway 46 and a low-impedance electrical pathway 48, wherein each of the electrical pathways 46, 48 is electrically coupled to a respective electrode 44 (e.g., the electrode $44_1$ is electrically coupled to the low-impedance electrical pathway 48, while the electrode $44_2$ is electrically coupled to the high-impedance electrical pathway 46). It will be appreciated, however, that in other exemplary embodiments, catheters having more or less than two electrodes 44, and/or more than one high-impedance electrical pathway 46 and/or low-impedance electrical pathway 48 (e.g., in an instance where there are three or more electrodes, each being electrically coupled to at least one of a high- and low-impedance electrical pathway, for example) remain within the spirit and scope of the present disclosure.

As briefly described above, the high-impedance electrical pathway 46 is configured to electrically couple the electrode $44_2$ with one or more subsystems 14 of the EP lab system 10, such as, for example, the visualization, navigation, and/or mapping system 16 and/or the EP monitoring and recording system 18 (both of which will be described in greater detail below), that allow for the transmission or communication of electrical signals thereto over high-impedance electrical pathways. In an exemplary embodiment, the high-impedance electrical pathway 46 will have an impedance on the order of a few kilo-ohms. More specifically, in an exemplary embodiment, the impedance of the high-impedance electrical pathway 46 is on the order of 2000 ohms (2 kΩ) or greater.

In one exemplary embodiment, the high-impedance electrical pathway 46 comprises a high-impedance conductor. More particularly, in such an embodiment, the high-impedance electrical pathway 46 comprises a conductor formed of a non-ferromagnetic metal alloy that may include, for example and without limitation, one or more of: a nickel-chrome alloy (NiCr), a nickel-iron alloy (NiFe), a copper-nickel alloy (CuNi), and a manganese-nickel-copper alloy (MnNiCu). In any event, the high-impedance conductor, regardless of the material, will have a resistance much greater than that of a copper conductor (e.g., as much as 100 times that of a similarly-sized copper conductor).

In another exemplary embodiment, the high-impedance electrical pathway 46 comprises a plurality of non-ferromagnetic conductor segments 50 having one or more resistive elements, such as, for example, the resistors 52 illustrated in FIGS. 2A and 2B, electrically coupled in series between respective pairs of conductor segments 50. The particular number of discrete resistors 52 that are needed will largely depend on the desired impedance of the high-impedance electrical pathway 46. Accordingly, the high-impedance electrical pathway 46 may contain one or more resistors to meet the desired impedance.

As also briefly described above, the low-impedance electrical pathway 48 is configured to electrically couple the electrode $44_1$ with one or more subsystems 14 of the EP lab system 10, such as, for example, the contact sensing system 20, the ablation system 22, and the EP stimulation system 24 (each of which will be described in greater detail below), that allow for or require the transmission or communication of electrical signals thereto, and delivery of electrical energy therefrom, over low-impedance electrical pathways.

Because the impedance of the low-impedance electrical pathway 48 is so low, unlike the high-impedance electrical pathway 46, the impedance of the low-impedance electrical pathway 48 alone is not sufficient to counteract the effects of the components of the MRI system described above. Accordingly, other steps must be taken to account for high RF currents that can be induced in the electrical pathway 48 due to antenna resonance caused by the magnetic resonance RF pulses. More particularly, at or near resonance, standing waves exist with areas of very high current. For magnetic resonance RF pulses at approximately 63.9 MHz, a quarter wave antenna has a length of about 110 cm, or about the length of many catheters, and counting cables and connectors, conductors are likely to resonate at $$n * \frac{\lambda}{4}.$$

This resonance may be prevented by either (i) increasing the impedance of the electrical pathway, or (ii) incorporating inductive elements into the low-impedance electrical pathway 48 at intervals less than $$\frac{\lambda}{4}.$$

Therefore, in most instances, one or two inductive elements may be used to negate the likelihood of resonance within the electrical pathway 48, and thus, the negative effects caused thereby.

Accordingly, as illustrated in FIGS. 2A and 2B, the low-impedance electrical pathway 48 may include one or more inductive elements 54, which may comprise an inductor or a choke, for example, configured to attenuate magnetic resonance RF pulses while allowing other electrical signals or energy to pass through with little loss. In one exemplary embodiment, the inductive elements 54 comprise small surface mount devices (e.g., having exemplary dimensions of 0.5×0.5×1.0 mm). In another exemplary embodiment, the inductive elements 54 may comprise loops of wire wrapped around a core, such as, for example, the shaft 38 of the catheter 12 or another material having high magnetic permeability. In another exemplary embodiment, the inductive elements 54 may comprise a pair of counter-wound inductors. In still another exemplary embodiment, the inductive elements 54 may comprise inductors that may be utilized in adjacent pairs of opposite polarity so that the rapidly changing magnetic resonance RF and magnetic resonance gradient pulses are not coupled into the pathway 48 by the inductors themselves, but instead the resulting pathway currents are suppressed. In addition to the inductive elements 54, the low-impedance electrical pathway 48 may further comprise a plurality of low impedance, non-ferromagnetic electrical conductors 56 having one or more inductive elements 54 electrically coupled in series between respective pairs of the conductor segments 56. In any event, in an exemplary embodiment, the series inductance of the low-impedance electrical pathway 48 may be on the order of approximately 1-2.5 microhenries (1-2.5 μH).

In certain instances, it may be desirable to electrically couple the electrode $44_1$ to a subsystem 14 of the EP lab system 10 to which the electrode $44_2$ is also electrically coupled through the high-impedance electrical pathway 46. For example, it may be desirable to provide a position signal generated or sensed by the electrode $44_1$ to the visualization, navigation, and/or mapping system 16. In such an instance, because the electrode $44_2$ is electrically coupled to the system 16 via a high-impedance electrical pathway, and the electrode $44_1$ is electrically coupled via a low-impedance electrical pathway, steps must be taken to make the inputs to the system 16 consistent in order to avoid offsets in electrode positions determined from data acquired by different electrodes corresponding to electrical pathways of different impedances.

With reference to FIG. 2B, one way in which this may be done is to electrically connect an impedance element 58, such as, for example, a resistor of an appropriate value in series between the low-impedance electrical pathway 48 and either the subsystem 14, or, as will be described below, the interface module 26, of the EP lab system 10 to provide a high-impedance electrical pathway for those corresponding electrical signals. It will be appreciated that while in the embodiment described above the impedance element 58 comprises a resistor, the present disclosure is not meant to be so limited. Rather, in other exemplary embodiments, the impedance element 58 may comprise any number of impedance elements, such as, for example, a series combination of a resistor and capacitor of appropriate values. Accordingly, the present disclosure is not meant to be limited to any one type of impedance element. Further, in alternative embodiments, such as that described below, steps may be taken to alter or adjust the signals communicated through the high-impedance electrical pathway 46 rather than including the series impedance element 58 in the low-impedance electrical pathway 48.

As briefly described above, in addition to the catheter 12, the EP lab system 10 may further comprise one or more diagnostic and/or therapeutic subsystems 14 to which the catheter 12, and the electrode(s) 44 and/or other components thereof, in particular, are electrically coupled. These subsystems 14 may receive and process signals generated or sensed by the electrode(s) 44, for example, and/or generate and transmit electrical signals or energy to the electrode(s) 44 for application to desired anatomic structures (i.e., the tissue 28). A number of exemplary subsystems 14 will now be briefly described.

One subsystem 14 is the visualization, navigation, and/or mapping system 16. The system 16 is provided for visualization, navigation, and/or mapping of internal body structures. The system 16 may comprise an electric field-based system, such as, for example, the EnSite™ NavX™ system commercially available from St. Jude Medical, Inc., and as generally shown with reference to U.S. Pat. No. 7,263,397, the entire disclosure of which is incorporated herein by reference. In other exemplary embodiments, however, the system 16 may comprise systems other than electric field-based systems. For example, the system 16 may comprise a magnetic field-based system such as the Carto™ system commercially available from Biosense Webster, and as generally shown with reference to one or more of U.S. Pat. Nos.: 6,498,944; 6,788,967; and 6,690,963, the entire disclosures of which are incorporated herein by reference. In another exemplary embodiment, the system 16 may comprise a magnetic field-based system such as the MediGuide™ Technology system commercially available from MediGuide Ltd., and as generally shown with reference to one or more of U.S. Pat. Nos.: 6,233,476; 7,197,354; and 7,386,339, the entire disclosures of which are incorporated herein by reference. In yet another embodiment, the system 16 may comprise a combination electric field-based and magnetic field-based system, such as, for example and without limitation, the Carto 3™ system also commercially available from Biosense Webster. For purposes of clarity and illustration only, the system 16 will be described hereinafter as comprising an electric field-based system, such as, for example, the EnSite™ NavX™ system identified above.

With reference to FIG. 1, the visualization, navigation, and/or mapping system 16 may include, among other components, a plurality of patch electrodes 60, an electronic control unit (ECU) 62, and a display device 64. However, it will be appreciated that in another exemplary embodiment, the ECU 62 and/or the display device 64 may be separate and distinct components from the system 16 that are electrically coupled to, and configured for communication with, the system 16.

Figure 3:
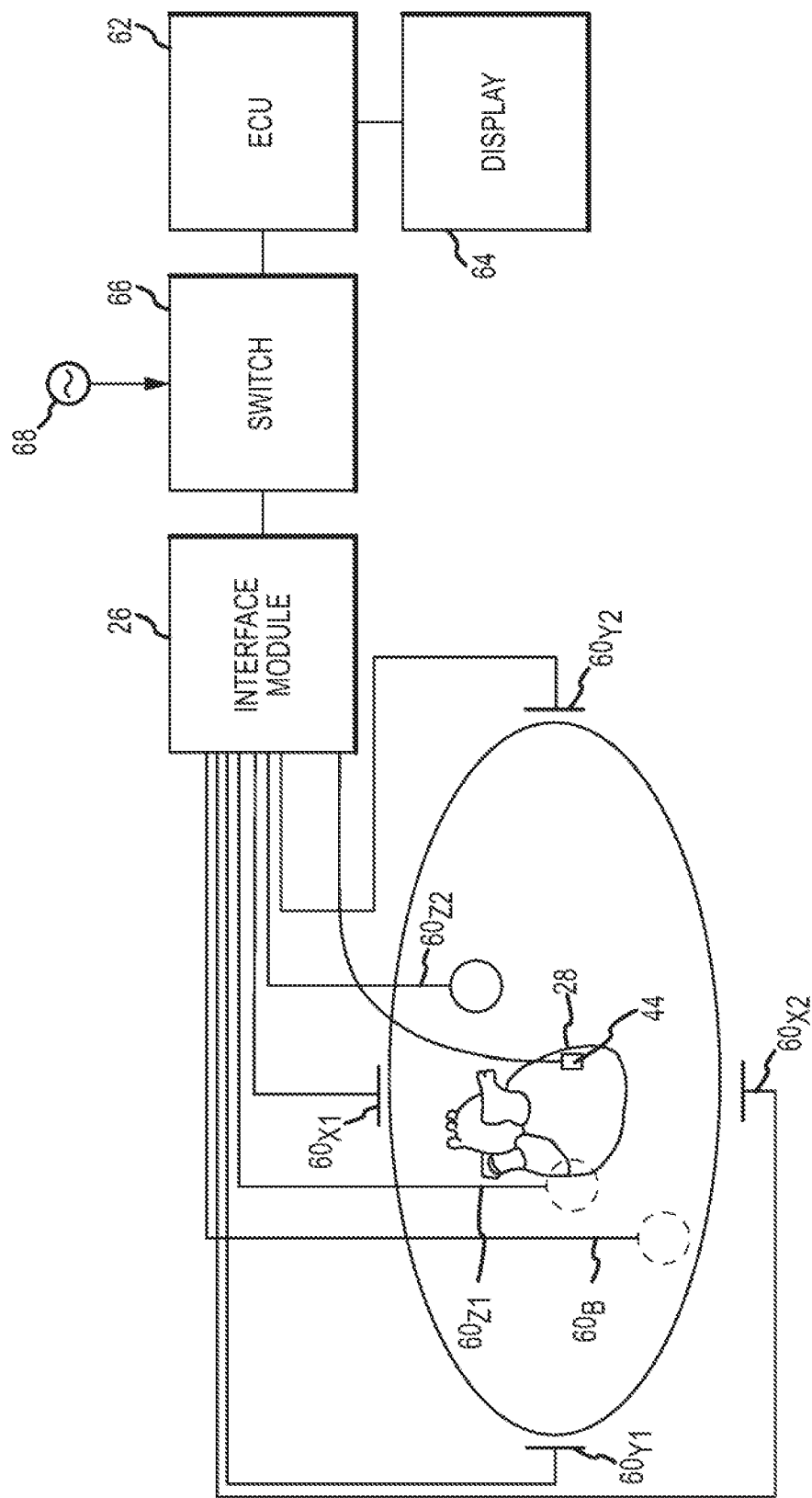
FIG. 3 is a simplified schematic view of an exemplary visualization, navigation, and/or mapping system of the EP lab system illustrated in FIG. 1.

With reference to FIG. 3, with the exception of the patch electrode $60_B$ called a "belly patch," the patch electrodes 60 are provided to generate electrical signals used, for example, in determining the position and orientation of the catheter 12 and in the guidance thereof. In one embodiment, the patch electrodes 60 are placed orthogonally on the surface of the body 14 and are used to create axes-specific electric fields within the body of the patient. For instance, in one exemplary embodiment, patch electrodes $60_{X1}$, $60_{X2}$ may be placed along a first (x) axis. Patch electrodes $60_{Y1}$, $60_{Y2}$ may be placed along a second (y) axis, and patch electrodes $60_{Z1}$, $60_{Z2}$ may be placed along a third (z) axis. Each of the patch electrodes 60 may be coupled to a multiplex switch 66. In an exemplary embodiment, the ECU 62 is configured, through appropriate software, to provide control signals to switch 66 to thereby sequentially couple pairs of electrodes 60 to a signal generator 68. Excitation of each pair of electrodes 60 generates an electrical field within the body and within an area of interest such as the tissue 28. Voltage levels at non-excited electrodes 60, which are referenced to the belly patch $60_B$, are filtered and converted and provided to the ECU 62 for use as reference values.

As briefly discussed above, the catheter 12 includes one or more electrodes 44 mounted therein or thereon. In an exemplary embodiment, at least one of the electrodes, electrode $44_2$, for example, comprises a positioning electrode and is configured to be electrically coupled to the ECU 62, through, as will be described below, the interface module 26 of the EP lab system 10. With the positioning electrode $44_2$ electrically coupled to the ECU 62, the positioning electrode $44_2$ is placed within electrical fields created in the body (e.g., within the heart) by exciting the patch electrodes 60. The positioning electrode $44_2$ experiences voltages that are dependent on the location between the patch electrodes 60 and the position of the positioning electrode $44_2$ relative in the tissue 28 relative to electrode $60_B$. Voltage measurement comparisons made between the electrode $44_2$ and the patch electrodes 60 can be used to determine the position of the positioning electrode $44_2$ relative to the tissue 28. Movement of the positioning electrode $44_2$ proximate the tissue 28 (e.g., along the surface of a heart chamber) produces information regarding the geometry of the tissue 28. This information may be used, for example, to generate models and maps of anatomical structures. Information received from the positioning electrode $44_2$ can also be used to display on a display device, such as the display device 64, the location and orientation of the positioning electrode $44_2$ and/or the tip of the catheter 12 relative to the tissue 28. Accordingly, among other things, the ECU 62 of the system 16 provides a means for generating display signals used to the control display device 64 and the creation of a graphical user interface (GUI) on the display device 64.

In addition to the above, the ECU 62 may further provide a means for controlling various components of system 16 including, but not limited to, the switch 66. It should be noted that while in an exemplary embodiment the ECU 62 is configured to perform some or all of the functionality described above and below, in other exemplary embodiments, the ECU 62 may be separate and distinct from the system 16, and/or the system 16 may have another processor (e.g., another ECU) configured to perform some or all of the functionality described herein. In such an embodiment, the processor of the system 16 would be electrically coupled to, and configured for communication with, the ECU 62. However, for purposes of clarity and illustration only, the description below will be limited to an embodiment wherein ECU 62 is part of system 16 and configured to perform all of the functionality described herein.

The ECU 62 may comprise a programmable microprocessor or microcontroller, or may comprise an application specific integrated circuit (ASIC). The ECU 62 may include a central processing unit (CPU) and an input/output (I/O) interface through which the ECU 62 may receive a plurality of input signals including, for example, signals generated by patch electrodes 60 and the positioning electrode $44_2$ (among others), and generate a plurality of output signals including, for example, those used to control the display device 64 and the switch 66. The ECU 62 may be configured to perform various functions, such as those described in greater detail above and below, with appropriate programming instructions or code (i.e., software). Accordingly, the ECU 62 is programmed with one or more computer programs encoded on a computer-readable storage medium for performing the functionality described herein.

In operation, the ECU 62 generates signals to control the switch 66 to thereby selectively energize the patch electrodes 60. The ECU 62 receives position signals (location information) from the catheter 12 (and particularly the positioning electrode $44_2$) reflecting changes in voltage levels on the positioning electrode $44_2$ and from the non-energized patch electrodes 60. The ECU 62 uses the raw positioning data produced by the patch electrodes 60 and positioning electrode $44_2$ and corrects the data to account for respiration, cardiac activity, and other artifacts using known or hereinafter developed techniques. The corrected data may then be used by the system 16 (e.g., the ECU 62) in a number of ways, such as, for example and without limitation, to create a model of an anatomical structure, to map electrophysiological data on an image or model of the tissue 28 generated or acquired by the ECU 62, for example, or to create a representation of the catheter 12 that may be superimposed on a map, model, or image of the tissue 28 generated or acquired by the ECU 62, for example.

The display device 64, which, as described above, may be part of the system 16 or a separate and distinct component, is provided to convey information to a clinician. The display device 64 may comprise a conventional computer monitor or other display device. The display device 64 presents a graphical user interface (GUI) to the clinician. The GUI may include a variety of information including, for example and without limitation, an image or model of the geometry of the tissue 28, EP data associated with the tissue 28, EGMs, ablation data associated with the tissue 28 and/or the ablation system 22, electrocardiographic maps, and images of the catheter 12 and/or one or more electrodes 44 thereof. Some or all of this information may be displayed separately (i.e., on separate screens or windows) or simultaneously. The GUI may further provide a means by which a clinician may input information or selections relating to various features of the system 16 into the ECU 62.

The image or model of the geometry of the tissue 28 may comprise a two-dimensional image of the tissue 28 (e.g., a cross-section of the heart) or a three-dimensional image of the tissue 28. The image or model may be generated by the system 16 (e.g., the ECU 62), or alternatively, may be generated by another imaging, modeling, or visualization system (e.g., fluoroscopic, computed tomography (CT), magnetic resonance imaging (MRI), direct visualization, etc. based systems) that are communicated to, and therefore, acquired by, the ECU 62. As briefly mentioned above, the display device 64 may also include an image of the catheter 12 and/or one or more electrodes 44 thereof illustrating their position relative to the tissue 28. The image of the catheter may be part of the image itself or may be superimposed onto the image/model.

With reference to FIG. 1, another exemplary subsystem 14 that the EP lab system 10 may include is the EP monitoring and recording system 18. The system 18 is provided and configured to receive, digitize, display, and store data, such as, for example, EGMs, sensed or acquired by one or more electrodes 44 of the catheter 12, or data provided by other components or subsystems 14 of the EP lab system 10, such as, for example, the ablation system 22. The system 18 may comprise conventional apparatus well known in the art. In one exemplary embodiment, the system 18 may comprise the EP-WorkMate™ system commercially available from St. Jude Medical, Inc. The system 18 can be configured to record a number of intracardiac channels, and may include a display device (not shown) to allow for the viewing of the data monitored and recorded by the system 18. Alternatively, the display device 64 of the visualization, navigation, and/or mapping system 16 may be configured to display the data. As will be described in greater detail below, the system 18 and the corresponding electrode(s) 44 may be electrically coupled together through the interface module 26 of the EP lab system 10.

As briefly described above, another subsystem 14 that may be included in the EP lab system 10 is a tissue contact sensing system 20. The system 20 is provided and configured to sense or determine, for example, the degree of contact between an electrode 44, such as, for example, the electrode $44_2$, and tissue, such as, for example, the tissue 28. More particularly, in an exemplary embodiment, using a combination of patch electrodes, such as, for example, the patch electrodes of the ablation system 22 to be described below or the visualization, navigation, and/or mapping system 16, and one or more catheter mounted electrodes 44, the system 20 is configured to acquire values for one or more components of the complex impedance between an electrode 44 and the tissue 28, and to calculate an electrical coupling index (ECI) responsive thereto. The raw ECI may then be displayed on a display device for use by a clinician in determining degree of contact between the catheter 12 and the tissue 28. Alternatively, the raw ECI may be processed by a processor or electronic control unit, such as, for example, the ECU 62 of the visualization, navigation, and/or mapping system 16 to assess the degree of contact. For purposes of clarity and illustration, the description below will be with respect to an embodiment wherein the ECU 62 of the system 16 is configured to process the ECI data and to assess the degree of contact between the catheter 12 and the tissue 28. It will be appreciated, however, that in other exemplary embodiments that remain within the spirit and scope of the present disclosure, another processor that is part of the system 20 or otherwise may be used for this purpose rather than the ECU 62.

A detailed description of an exemplary approach of calculating the ECI and assessing the degree of contact is set forth in U.S. Patent Publication No. 2009/0163904 filed May 30, 2008, the entire disclosure of which is incorporated herein by reference. To summarize, however, and with reference to FIG. 4, the system 20 may include a tissue sensing circuit comprising a tissue sensing signal source 70 configured to generate an excitation signal used in impedance measurements, and means, such as a complex impedance sensor 72, for resolving detected impedance into its component parts.

The signal source 70 is configured to generate one or more excitation signals across a pair of source connectors (e.g., across an electrode 44 and a patch electrode disposed on the patient). In an exemplary embodiment, the electrical connection between the signal source 70 and the source connectors may be a direct connection, while in another embodiment, and as will be described below, the connection is made through the interface module 26. The signal source 70 may output a signal having a frequency within a range from about 1 kHz to over 500 kHz, more preferably within a range of about 2 KHz to 200 kHz, and even more preferably about 20 kHz. In an exemplary embodiment, the excitation signal is a constant current signal, preferably in the range of between 20-200 µA, and more preferably about 100 µA. The constant current AC excitation signal generated by the signal source 70 is configured to develop a corresponding AC response voltage signal that is dependent on the complex impedance of the tissue 28 and is sensed by the complex impedance sensor 72, which is electrically coupled across a pair of sense connectors (e.g., across an electrode 44 and a patch electrode disposed on the patient). As with the signal source connections described above, in an exemplary embodiment, the electrical connection between the complex impedance sensor 72 and the sense connectors may be a direct connection, while in another exemplary embodiment, and as will be described below, the connection is made through the interface module 26. The sensor 72 resolves the impedance into its component parts, namely, resistance (R) and reactance (X), or the impedance magnitude ($\|Z\|$) and phase angle ($\angle Z$ or $\phi$).

In any event, one or more components of the complex impedance may then be used by the ECU 62, or another processor of the system 20 or EP lab system 10, to calculate the ECI. For example, in one embodiment provided for exemplary purposes only, the ECI is calculated using the equation (1):

$$\text{ECI}=a*R\text{mean}+b*X\text{mean}+c \qquad (1)$$

wherein Rmean is the mean value of a plurality of resistance values, Xmean is the mean value of a plurality of reactance values, and a, b, and, c are coefficients dependent upon, among other things, the specific catheter used, the patient, the equipment, the desired level of predictability, the species being treated, and disease states. More specifically, for one particular 4 mm irrigated tip catheter, the ECI is calculated using the equation (2):

$$\text{ECI}=R\text{mean}-5.1*X\text{mean} \qquad (2)$$

It should be understood that variations are contemplated by the present disclosure. For example, the excitation signal generated by the signal source 70 may be an AC voltage signal (as opposed to an AC current signal described above) where the response signal comprises an AC current signal. Nonetheless, a constant current excitation signal is preferred as being more practical. It should be appreciated that the excitation signal frequency is preferably outside of the frequency range of ablation signals, which are the order of 400-500 MHz, and expected EGM signals, which are on the order of 0.05 Hz-1 kHz, to allow the complex impedance sensor 72 to readily distinguish between the various types of signals. Additionally, in certain embodiments, multiple excitation signals of different frequencies may be used to determine multiple complex impedances. For example, a 20 kHz signal and a 200 kHz signal may be generated and a complex impedance corresponding to each may be determined and used. Accordingly, the present disclosure is not meant to be limited to an embodiment wherein a single excitation signal is employed, but rather includes embodiments wherein multiple excitation signals are used Yet another subsystem 14 that may be included in the EP lab system 10 is the ablation system 22. The system 22 is provided and configured to deliver therapy to tissue in the form of, for example, electrical energy. With reference to FIG. 1, in an exemplary embodiment, the ablation system 22 comprises, among other components, one or more patch electrodes 74 (e.g., patch electrodes $74_1$-$74_3$) and an ablation generator 76.

In an exemplary embodiment such as that illustrated in FIG. 1, the patch electrode $74_1$ is configured to be applied to the patient's skin and may function as an RF indifferent/dispersive return for an RF ablation signal generated by the ablation generator 76. The patch electrodes $74_2$, $74_3$ are also configured to be applied to the patient's skin and may function as returns for the RF ablation signal source and/or, in an exemplary embodiment, an excitation signal generated by the tissue sensing circuit of the tissue contact sensing system 20 described above (not shown). The patch electrodes $74_2$, $74_3$ may be spaced relatively far apart from each other. For example, in the illustrated embodiment, the electrodes $74_2$, $74_3$ are located on the medial aspect of the patient's left leg and the dorsal aspect of the neck, respectively. The electrodes $74_2$, $74_3$ may alternatively be located on the front and back of the torso or in other conventional arrangements or orientations.

The ablation generator 76 generates, delivers, and controls RF energy output by the catheter 12, and an ablation element or electrode 44 thereof, in particular (e.g., the electrode $44_1$). The generator 76 is conventional in the art and may comprise the commercially available unit sold under the model number IBI-1500T-11 RF Cardiac Ablation Generator, available from Irvine Biomedical, Inc. The generator 76 includes an RF ablation signal source configured to generate an ablation signal that is output across a pair of source connectors: a positive polarity connector which may be electrically coupled to a catheter-mounted electrode such as the electrode $44_1$; and a negative polarity connector which may be electrically coupled by conductors or lead wires to one of the patch electrodes 74. It should be understood that the term "connectors" as used herein does not imply a particular type of physical interface mechanism, but is rather broadly contemplated to represent one or more electrical nodes.

The ablation signal source is configured to generate a signal at a predetermined frequency in accordance with one or more user-specified parameters (e.g., power, time, etc.) and under the control of various feedback sensing and control circuitry as is known in the art. The source may generate a signal, for example, with a frequency of about 450 kHz or greater. The generator 76 may also monitor various parameters associated with the ablation procedure including impedance, the temperature at the ablation electrode 44, ablation energy, and the position of the catheter and provide feedback to the clinician or other components of the EP lab system 10 regarding these parameters. Accordingly, the generator 76 may transmit electrical energy to perform ablation procedures, and also receive electrical signals corresponding to one or more parameters related thereto.

In addition to one or more of the subsystems 14 described above, or in the alternative, the EP lab system 10 may further comprise the cardiac stimulation system 24 (or stimulator 24). The stimulator 24 is configured to provide electrical stimulation or pacing of the heart. The stimulator 24 may comprise a stand-alone system or can be integrated with another component of the EP lab system 10, such as, for example and without limitation, the monitoring and recording system 18. The stimulator 24 is configured to allow a user to initiate or terminate tachyarrhythmias manually or automatically using preprogrammed modes of operation. The stimulator 24 may comprise conventional apparatus known in the art. In an embodiment, the stimulator 24 can comprise a commercially available cardiac stimulator sold under the trade designation EP-4™ available from St. Jude Medical, Inc. Accordingly, in operation, the stimulator 24 is electrically coupled to an electrode 44 of the catheter 12, such as, for example, the electrode $44_1$ to allow for the delivery of electrical stimulation/pacing signals generated by the stimulator 24 to the tissue 28. The stimulator 24 may further comprise a display device, or be electrically coupled to another display device of the EP lab system 10, such as, for example, the display device 64, to display the output of the stimulator 24.

As briefly described above, and as illustrated in FIGS. 1 and 4, the EP lab system 10 may further comprise an interface model 26 disposed between the catheter 12 and one or more subsystems 14 of the EP lab system 10. The interface module 26 is configured to electrically couple the electrodes 44 of the catheter 12, and in certain embodiments, other components of the catheter 12 such as, for example, thermistors or thermocouples disposed at or near the distal portion 42 thereof, to one or more of the subsystems 14 (either directly or through interface or input/signal processing circuitry thereof). In an exemplary embodiment, the interface module 26 is also disposed between one or more patch electrodes of the visualization, navigation, and/or mapping system 16 and/or the ablation system 22 and is configured to electrically couple the one or more patch electrodes with one or more subsystems 14. As such, in an exemplary embodiment, the interface module 26 is disposed in close proximity to the patient, such as, for example, next to or near the patient's bed (e.g., bedside).

As with the high- and low-impedance electrical pathways 46, 48 of the catheter 12, the interface module 26 is provided to render the EP lab system 10 compatible with MRI systems to allow the EP lab system 10 to be used in conjunction with an MRI system. More particularly, the interface module 26 is provided and configured to protect the instrumentation of the subsystems 14 of the EP lab system 10 and electrical signals transmitted or communicated through the EP lab system 10 from the effects of the MRI components described above, and the magnetic resonance RF and gradient field pulses, in particular.

Figure 4:
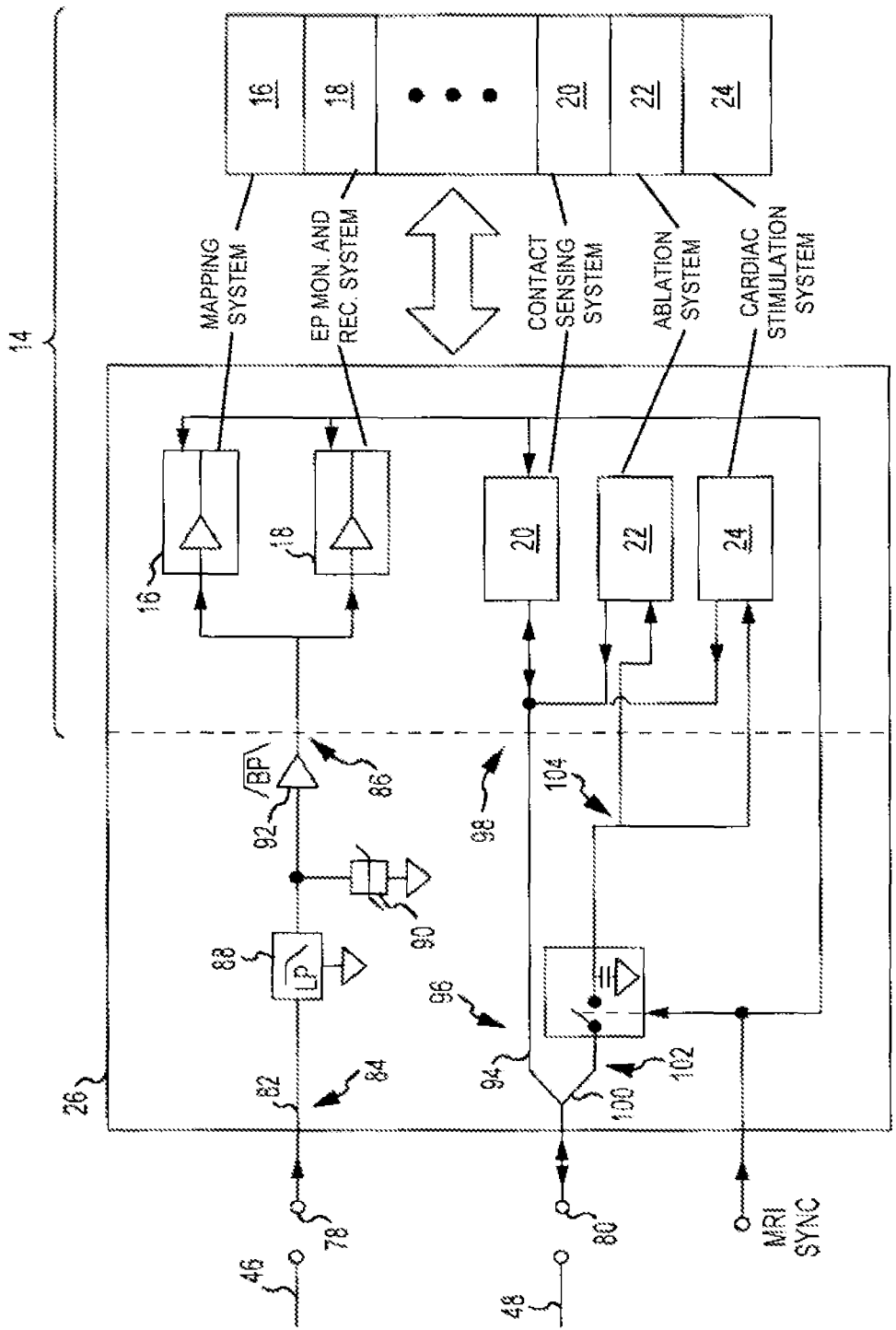
FIG. 4 is a diagrammatic and schematic view of an exemplary interface module of the EP lab system illustrated in FIG. 1.

In an exemplary embodiment, the interface module 26 comprises at least one high-impedance channel 78 comprising one or more electrical pathways configured to be electrically coupled with one or more high-impedance electrical pathways 46 of the catheter 12. The interface module 26 further comprises at least one low-impedance channel 80 comprising one or more electrical pathways configured to be electrically coupled with one or more low-impedance electrical pathways 48 of the catheter 12. For purposes of clarity and illustration, the description below will be limited to an embodiment wherein the interface module 26 comprises a single high-impedance channel 78 and a single low-impedance channel 80. It will be appreciated, however, that in other exemplary embodiments, the interface module 26 may comprise any number of high- and/or low-impedance channels, and therefore, embodiments wherein the interface module 26 comprises two or more high- and/or low-impedance channels configured to be electrically coupled with the catheter 12 remain within the spirit and scope of the present disclosure. With reference to FIG. 4, each of the high- and low-impedance channels 78, 80 will be described in turn below.

As illustrated in FIG. 4, in an exemplary embodiment, the high-impedance channel 78 comprises an electrical pathway 82 having a first end 84 and a second end 86. The first end 84 is configured to be electrically coupled to one or more high-impedance electrical pathways 46 of the catheter 12. The second end 86 is configured to be electrically coupled to one or more subsystems 14 of the EP lab system 10 (e.g., the visualization, navigation, and/or mapping system 16, the monitoring and recording system 18, etc.), or to input or signal processing circuitry (hereinafter referred to as "interface circuitry") thereof that is configured to condition or otherwise preprocess the electrical signals (e.g., amplifiers, filters, and/or other signal processing circuitry) prior to transmission to the corresponding subsystems 14. In an exemplary embodiment wherein the second end 86 of the electrical pathway 82 is electrically coupled to interface circuitry of one or more subsystems 14, the interface circuitry may be part of the interface module 26 (i.e., within the same housing, for example) or separate and distinct therefrom. Further, in an embodiment wherein the second end 86 of the electrical pathway 82 is electrically coupled directly to one or more components of one or more subsystems 14, those components may be part of the interface module (i.e., within the same housing, for example) or separate and distinct therefrom. In any event, components of the respective subsystems 14 (e.g., user interfaces or controls, display devices or workstations, etc.) may be located away from the interface module 26 and/or other components or interface circuitry thereof (e.g., outside of the magnetic field generated by the MRI system), and may be electrically coupled thereto by, for example, fiber optic cables.

In an exemplary embodiment, the electrical pathway 82 is configured to attenuate magnetic resonance RF and gradient field pulses generated by the MRI system. More particularly, the electrical pathway 82 may be comprised of discrete, known-in-the-art electrical components electrically coupled together by electrical conductors. More specifically, in the illustrated embodiment, the electrical pathway 82 comprises a low pass filter 88 disposed at or near the first end 84 thereof. The low pass filter 88 is configured to attenuate magnetic resonance RF pulses generated in the MRI system. More particularly, when the catheter 12 is coupled with the interface module 26, the input side of the low pass filter 88 is electrically coupled to the high-impedance electrical pathway 46 of the catheter 12. The low pass filter 88 is configured to allow certain electrical signals, such as, for example, EGMs having frequencies between around 0.05 Hz-1 kHz and positioning signals having frequencies between around 4-12 kHz, to pass therethrough with little loss or distortion, while attenuating magnetic resonance RF pulses having frequencies on the order of 63.9 MHz. To account for the magnetic resonance gradient pulses, which may be brief and relatively large in magnitude, in an exemplary embodiment, the electrical pathway 82 may further comprise a limiter or clamp circuit 90. As illustrated in FIG. 4, the input side of the limiter circuit 90 is electrically coupled in series to the output side of the low pass filter 88.

In an exemplary embodiment, in addition to, or instead of, including one or both of the low pass filter 88 and the limiter circuit 90, the electrical pathway 82 or the subsystem(s) 14 or the interface circuitry thereof may further include a means to invoke a blanking function or other temporal mechanisms configured to suppress artifacts caused by the magnetic resonance gradient field pulses and/or the magnetic resonance RF pulses. To that end, in an exemplary embodiment, the pathway 82 may further include an interrupter circuit (not shown), such as, for example, a track-or-hold circuit comprising a switched capacitor. The interrupter circuit may receive a signal to synchronize the sensing functions of the subsystem(s) 14 with the magnetic resonance sequence of the MRI system. For example, in an exemplary embodiment, the interrupter circuit may receive as an input a "sync" signal generated by the MRI system to synchronize the sensing functions of the subsystem(s) 14 with the magnetic resonance sequence of the MRI system.

More particularly, when there are no magnetic resonance gradient field pulses (and possibly magnetic resonance RF pulses), the sync signal causes a switch of the circuit to close and the sensing or tracking function of the electrical signals proceeds normally. In such an instance, the capacitor of the circuit may provide a certain degree of low pass filtering. However, in response to magnetic resonance gradient field pulses (and possibly magnetic resonance RF pulses), the sync signal may cause the switch to momentarily open to disconnect the subsystem(s) 14 from the pathway 82 and the sensed or tracked electrical signal is effectively held by the capacitor until the switch is once again closed. As a result, the sensing function(s) of the subsystem(s) 14 operate largely unchanged.

While the description above is with respect to an embodiment wherein the sync signal is generated by the MRI system, it will be appreciated that the present disclosure is not meant to be so limited. Rather, in other exemplary embodiments, the sync signal may be generated by a sync signal generator comprising circuitry or components other than the MRI system. For instance, the system 10 (e.g., the interface module 26 or one or more subsystems 14 thereof) may comprise an analog circuit, such as, for example, a differentiator configured to monitor the rate of change on an electrical pathway, such as, for example, an electrical pathway of one of the high- or low-impedance channels 78, 80. In such an embodiment, when the rate of change exceeds a certain predetermined threshold value, the circuit may produce a sync signal that may be used as described above.

In another embodiment, the system 10 (e.g., the interface module 26 or one or more subsystems 14 thereof) may comprise an analog comparator configured to monitor the voltage level on an electrical pathway, such as, for example, an electrical pathway of one of the high- or low-impedance channels 78, 80, and to produce a sync signal when the voltage exceeds a certain predetermined threshold value. As with the embodiment described immediately above, the sync signal may be used in the same manner described above.

In yet another embodiment, the system 10 (e.g., the interface module 26 or one or more subsystems 14 thereof) may comprise a dedicated analog sensor (e.g., a magnetic field sensor) configured to detect when gradient field pulses and/or the magnetic resonance RF pulses are applied by the MRI system, and to generate a sync signal when such pulses are detected. The generated sync signal may be used in the same manner described above.

In yet still another exemplary embodiment, a software or firmware component configured to monitor the digitized signal and to initiate specific action when the amplitude or rate of change of the signal exceeds a certain predetermined value may be used. Accordingly, it will be appreciated by those having ordinary skill in the art that the sync signal may be generated in any number of ways, each of which remains within the spirit and scope of the present disclosure.

As briefly described above with respect to the low-impedance electrical pathway 48, in certain instances, certain types of electrical signals (e.g., position signals being communicated or transmitted to the visualization, navigation, and/or mapping system 16, for example) may be communicated or transmitted to the same subsystem 14 of the EP lab system 10 over electrical pathways having different impedances. Accordingly, steps must be taken to make these electrical pathways consistent so that the electrical signals communicated or transmitted over an electrical pathway having one impedance do not contain offset artifacts compared with the electrical signals communicated or transmitted over an electrical pathway having another impedance.

As was described above and illustrated in FIG. 2B, one way by which this may be done is to convert the low-impedance electrical pathway 48 to a high-impedance electrical pathway for those particular electrical signals by including a series resistor 58 in the low-impedance electrical pathway 48. In another exemplary embodiment, however, the electrical pathway 82 of the high-impedance channel 78 may be converted to a low-impedance electrical pathway to make it consistent with the low-impedance electrical pathway 48, and therefore, the low-impedance channel 80. More particularly, in an exemplary embodiment, the high-impedance channel 78, and the electrical pathway 82 thereof, in particular, may comprise a high input impedance (high performance) amplifier or buffer 92 disposed at the second end 86 of the pathway 82, the output of which is electrically coupled to one or more subsystem(s) 14 or components or interface circuitry thereof. Accordingly, in the embodiment illustrated in FIG. 4, the input side of the amplifier 92 is electrically coupled to the output side of the limiter circuit 90, and the output side of the amplifier 92 is electrically coupled to one or more subsystem(s) 14 or interface circuitry thereof. The amplifier 92 is operatively configured to effectively lower the impedance of the electrical pathway 82 of the high-impedance channel 78. Alternatively, in another exemplary embodiment, if the electrical pathways vary in impedance value, but do so in a controlled and known manner, signal processing hardware and/or software may be used to adjust or compensate the electrical pathways to thereby render all electrical pathways consistent with each other.

As illustrated in FIG. 4, in an exemplary embodiment, the low-impedance channel 80 comprises a first electrical pathway 94 having a first end 96 and a second end 98, and a second electrical pathway 100 having a first end 102 and a second end 104. The first ends 96, 102 are configured to be electrically coupled to one or more low-impedance electrical pathways 48 of the catheter 12. The second ends 98, 104 are configured to be electrically coupled to one or more subsystems 14 of the EP lab system 10 (e.g., the tissue contact sensing system 20, the ablation system 22, the stimulator 24, etc.), or interface circuitry thereof configured to condition or otherwise preprocess the electrical signals (e.g., filters, amplifiers, or other signal processing circuitry, for example) prior to transmission or communication of the electrical signals between the catheter 12 and the corresponding subsystem(s) 14. In an exemplary embodiment wherein the second ends 98, 104 of the electrical pathways 94, 100 are electrically coupled to one or more subsystems 14 or interface circuitry thereof, certain components of the subsystem(s) 14 (e.g., signal sources, for example) or the interface circuitry may be part of the interface module 26 (i.e., within the same housing, for example) or separate and distinct therefrom. Whether the second ends 98, 104 of the electrical pathways 94, 100 are electrically coupled directly to the subsystem(s) 14 or to interface circuitry thereof, components of the respective subsystems 14 (e.g., user interfaces or controls, display devices, workstations, etc.) may be located away from the interface module 26 and/or other components or interface circuitry thereof (e.g., outside of the magnetic field generated by the MRI system) and may be electrically coupled thereto by, for example, fiber optic cables.

With continued reference to FIG. 4, the first electrical pathway 94 is configured to provide a direct and uninterrupted pathway between the subsystem(s) 14 and the catheter 12, and the low-impedance electrical pathway(s) 48 thereof, in particular. More particularly, the electrical pathway 94 is intended to provide a pathway over which electrical signals or energy can be delivered to one or more low-impedance electrical pathways 48 of the catheter 12 from one or more of the subsystems 14. For example, the tissue contact sensing system 20 may transmit or communicate the electrical activation signals described above to the low-impedance electrical pathway 48 over the first electrical pathway 94. Similarly, the ablation system 22 and the stimulator 24 may transmit or deliver ablative RF energy and electrical signals in the form of pacing current pulses, respectively, to the low-impedance electrical pathway 48 over the first electrical pathway 94. Such signals and/or electrical energy are largely immune to the MRI artifacts or components described above, and therefore, may be transmitted or communicated regardless of the operational state of the MRI system.

Due to the nature of some of the electrical signals sensed or generated by the electrodes 44 or other components of the catheter 12 (e.g., thermistors or thermocouples of the ablation system 22, etc.) corresponding to one or more of the subsystems 14, the first electrical pathway 94 may also provide a pathway over which signals sensed or generated by an electrode 44 or another component of the catheter 12 may be transmitted or communicated from the catheter 12, and the low-impedance electrical pathway 48 thereof, in particular, to one or more subsystems 14. For instance, in an exemplary embodiment such as that illustrated in FIG. 5, the tissue contact sensing system 20 is electrically coupled to the first electrical pathway 94 to provide a path over which the electrical signals representative of the complex impedance between one or more electrodes 44 and the tissue 28 may be communicated or transmitted from the electrode(s) 44 to the system 20 or interface circuitry thereof.

In such an embodiment, to provide protection from the various magnetic resonance artifacts described above, either the system 20 or interface circuitry thereof may include a means to invoke a blanking function or other temporal mechanisms configured to suppress artifacts caused by the magnetic resonance gradient field and/or RF pulses. In an exemplary embodiment, an interrupter circuit 106 similar to that described above with respect to the high-impedance channel 78 may be employed. More particularly, the interrupter circuit 106 may comprise, for example, a track-or-hold circuit comprising a switched capacitor, and is configured to effectively disconnect the system 20 from the electrical pathway 94. Due to the nature of the signals transmitted or communicated to the system 20, in an exemplary embodiment, the interrupter circuit 106 is implemented at a point or location in the electronics or circuitry of the system 20 that is after that which processes the electrical signals to resolve the complex impedance into its component parts. Accordingly, in such an embodiment, the interrupter circuit 106 may be electrically coupled to the output side of the impedance sensor 72 of the system 20.

In any event, in an exemplary embodiment, the interrupter circuit 106 may receive a signal to synchronize the sensing functions of the subsystem(s) 14 with the magnetic resonance sequence of the MRI system. For example, in an exemplary embodiment, the interrupter circuit 106 may receive as an input a "sync" signal generated by the MRI system to synchronize the sensing functions of the subsystem(s) 14 with the magnetic resonance sequence of the MRI system.

More particularly, when there are no magnetic resonance gradient field pulses (and possibly magnetic resonance RF pulses), the sync signal causes a switch of the circuit to close and the sensing or tracking function of the electrical signals proceeds normally. In such an instance, the capacitor of the circuit may provide a certain degree of low pass filtering. However, in response to magnetic resonance gradient field pulses (and possibly magnetic resonance RF pulses), the sync signal causes the switch to open to disconnect the system 20 from the electrical pathway 94 and the sensed or tracked electrical signal (or the most recent values of the complex impedance components) is/are effectively held by the capacitor until the switch is once again closed. As a result, the sensing function of the system 20 operates largely unchanged.

While the description above is with respect to an embodiment wherein the sync signal is generated by the MRI system, it will be appreciated that the present disclosure is not meant to be so limited. Rather, in other exemplary embodiments, the sync signal may be generated by a sync signal generator comprising circuitry or components other than the MRI system. For instance, the system 10 (e.g., the interface module 26 or one or more subsystems 14 thereof) may comprise an analog circuit, such as, for example, a differentiator configured to monitor the rate of change on an electrical pathway, such as, for example, an electrical pathway of one of the high- or low-impedance channels 78, 80. In such an embodiment, when the rate of change exceeds a certain predetermined threshold value, the circuit may produce a sync signal that may be used as described above.

In another embodiment, the system 10 (e.g., the interface module 26 or one or more subsystems 14 thereof) may comprise an analog comparator configured to monitor the voltage level on an electrical pathway and to produce a sync signal when the voltage exceeds a certain predetermined threshold value. As with the embodiment described immediately above, the sync signal may be used in the same manner described above.

In yet another embodiment, the system 10 (e.g., the interface module 26 or one or more subsystems 14 thereof) may comprise a dedicated analog sensor (e.g., a magnetic field sensor) configured to detect when the gradient field pulses and/or the magnetic resonance RF pulses are applied by the MRI system, and to generate a sync signal when such pulses are detected. The generated sync signal may be used in the same manner described above.

In yet still another exemplary embodiment, a software or firmware component configured to monitor the digitized signal and to initiate specific action when the amplitude or rate of change of the signal exceeds a certain predetermined value may be used. Accordingly, it will be appreciated by those having ordinary skill in the art that the sync signal may be generated in any number of ways, each of which remains within the spirit and scope of the present disclosure.

Figure 5:
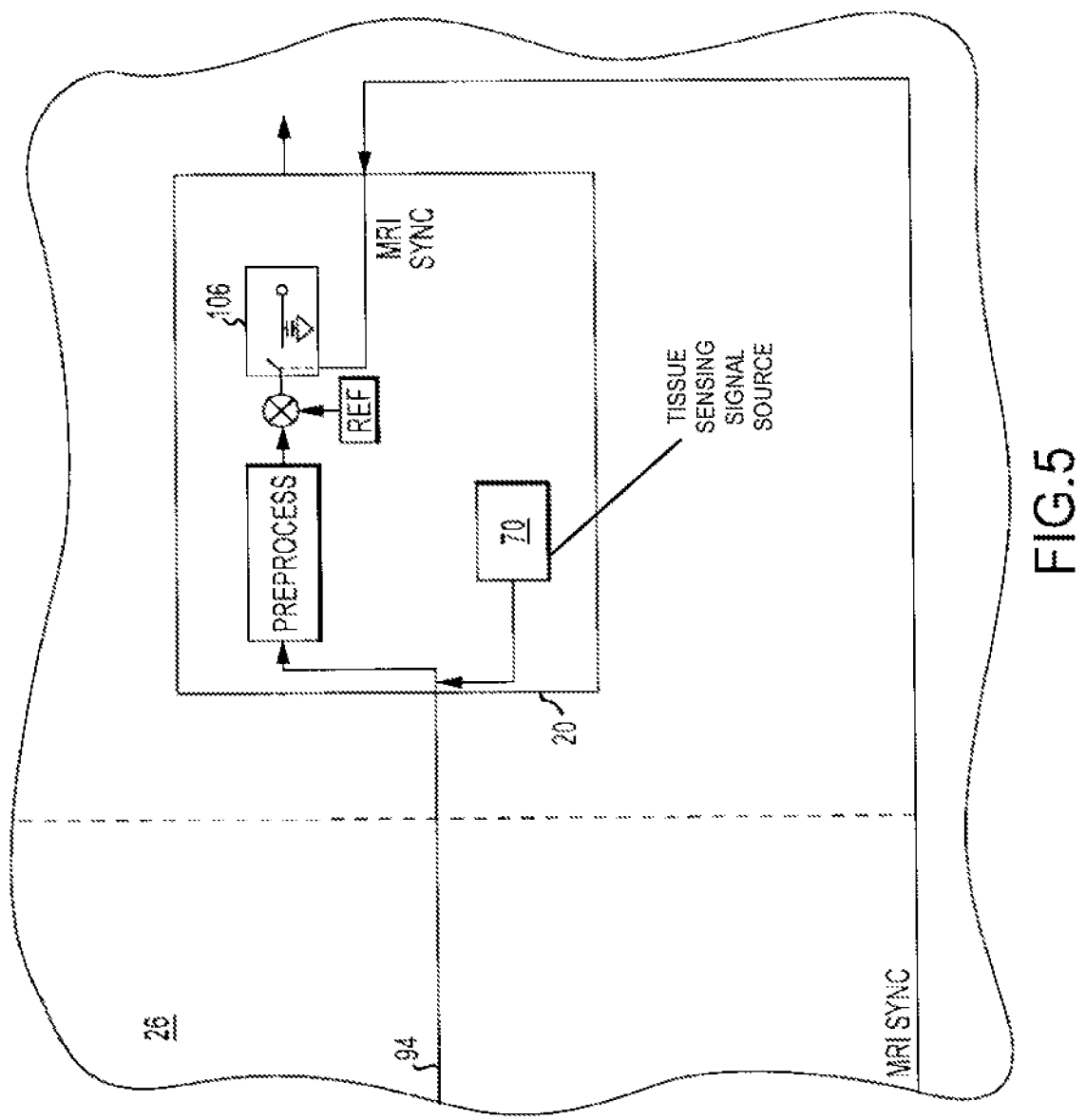
FIG. 5 is a diagrammatic and schematic view of an exemplary arrangement between the interface model illustrated in FIG. 4 and a portion of an exemplary tissue contact sensing system of the EP lab system illustrated in FIG. 1.

With reference to FIG. 5, because in this particular embodiment the interrupter circuit 106 is not disposed or implemented within the electrical pathway 94 of the interface module 26, the first electrical pathway 94 may provide a direct and uninterrupted path over which electrical signals may be transmitted from, and/or received by, the subsystems 14 of the EP lab system 10. As such, embodiments wherein the pathway 94 is configured to allow for the transmission and/or receipt of electrical signals from or by one or more subsystems 14 remain within the spirit and scope of the present disclosure.

With continued reference to FIG. 4, the second electrical pathway 100 is configured to provide an interruptable pathway between the subsystem(s) 14 and the catheter 12, and the low-impedance electrical pathway 48 thereof, in particular. More particularly, the second electrical pathway 100 is intended to provide a path through which electrical signals sensed or generated by one more electrodes 44 or other components of the catheter 12 (e.g., thermistors or thermocouples, for example) can be transmitted or communicated from the low-impedance electrical pathway 48 to one or more of the subsystems 14.

For example, and as is known in the art, the ablation system 22 may include impedance and/or temperature sense functions. Accordingly, one or more electrode(s) 44 and/or other components of the catheter 12 (e.g., thermistor(s) or thermocouple(s)) may be electrically coupled to the ablation system 22 through a combination of one or more low-impedance electrical pathways 48 of the catheter 12 and one or more low-impedance channels 80 of the interface module 26. More particularly, in an exemplary embodiment, the electrical signals representative of the sensed parameters are communicated or transmitted over the low-impedance electrical pathway 48 to the second electrical pathway 100 of the low-impedance channel 80, and then onto electronics or circuitry of the ablation system 22.

Similarly, in addition to generating and providing pacing or stimulation signals, the stimulator 24 may also include EGM sense functionality. Accordingly, one or more electrode(s) 44 of the catheter 12 may be electrically coupled to the stimulator 24 through a combination of one or more low-impedance electrical pathways 48 of the catheter 12 and one or more low-impedance channels 80 of the interface module 26. More particularly, in an exemplary embodiment, the electrical signals representative of the sensed EGM are communicated or transmitted over the low-impedance electrical pathway 48 to the second electrical pathway 100 of the low-impedance channel 80, and then onto electronics or circuitry of the stimulator 24.

As illustrated in FIG. 4, in order to protect the electrical signals representative of sensed parameters that are transmitted or communicated over the electrical pathway 100, as well as the subsystem(s) 14 and the components and/or interface circuitry thereof, from the various magnetic resonance components or artifacts described above, the electrical pathway 100 may include a means to invoke a blanking function or other temporal mechanisms to suppress artifacts caused by the magnetic resonance gradient field and/or RF pulses. To that end, the pathway 100 may include an interrupter circuit 108. More particularly, the interrupter circuit 108 may comprise, for example, a sample-and-hold circuit comprising a switched high-voltage capacitor and is configured to disconnect the subsystem(s) 14 and/or the certain components or interface circuitry thereof from the low impedance pathway 48 of the catheter 12. The particular value of the capacitor of the interrupter circuit 108 is dependent upon the particular signals being transmitted or communicated. More particularly, the value of the capacitor is chosen so as to not load down the transmitted signals. Accordingly, in an exemplary embodiment, the value of the capacitor may be determined using the equation:

$$C \le \frac{1}{2\pi f \cdot 10 \cdot |Z_{source}|},$$

wherein "f" is the frequency of the electrical signals and "$Z_{source}$" is the impedance of the corresponding signal source. In one embodiment provided for exemplary purposes only, the capacitor is an 800 nF capacitor.

In an embodiment, the interrupter circuit 108 receives a signal to synchronize the sensing functions of the subsystem(s) 14 with the magnetic resonance sequence of the MRI system. For example, in an exemplary embodiment, the interrupter circuit 108 may receive as an input a "sync" signal generated by the MRI system to synchronize the sensing functions of the subsystem(s) 14 with the magnetic resonance sequence of the MRI system.

More particularly, when there are no magnetic resonance gradient field pulses (and possibly magnetic resonance RF pulses), the sync signal causes a switch of the circuit to close and the sensing or tracking function of the electrical signals proceeds normally. In such an instance, the capacitor of the circuit may provide a certain degree of low pass filtering. However, in response to magnetic resonance gradient field pulses (and possibly magnetic resonance RF pulses), the sync signal causes the switch to open to disconnect the subsystem(s) 14 from the low-impedance electrical pathway 48 and the sensed or tracked electrical signal is effectively held by the capacitor until the switch is once again closed. As a result, the sensing function(s) of the subsystem(s) 14 operate largely unchanged.

While the description above is with respect to an embodiment wherein the sync signal is generated by the MRI system, it will be appreciated that the present disclosure is not meant to be so limited. Rather, in other exemplary embodiments, the sync signal may be generated by a sync signal generator comprising circuitry or components other than the MRI system. For instance, the system 10 (e.g., the interface module 26 or one or more subsystems 14 thereof) may comprise an analog circuit, such as, for example, a differentiator configured to monitor the rate of change on an electrical pathway, such as, for example, an electrical pathway of one of the high- or low-impedance channels 78, 80. In such an embodiment, when the rate of change exceeds a certain predetermined threshold value, the circuit may produce a sync signal that may be used as described above.

In another embodiment, the system 10 (e.g., the interface module 26 or one or more subsystems 14 thereof) may comprise an analog comparator configured to monitor the voltage level on an electrical pathway, such as, for example, an electrical pathway of one of the high- or low-impedance channels 78, 80, and to produce a sync signal when the voltage exceeds a certain predetermined threshold value. As with the embodiment described immediately above, the sync signal may be used in the same manner described above.

In yet another embodiment, the system 10 (e.g., the interface module 26 or one or more subsystems 14 thereof) may comprise a dedicated analog sensor (e.g., a magnetic field sensor) configured to detect when the gradient field pulses and/or the magnetic resonance RF pulses are applied by the MRI system, and to generate a sync signal when such pulses are detected. The generated sync signal may be used in the same manner described above.

In yet still another exemplary embodiment, a software or firmware component configured to monitor the digitized signal and to initiate specific action when the amplitude or rate of change of the signal exceeds a certain predetermined value may be used. Accordingly, it will be appreciated by those having ordinary skill in the art that the sync signal may be generated in any number of ways, each of which remains within the spirit and scope of the present disclosure.

In addition to the protection measures described above, in an exemplary embodiment, the electrical pathway 100 may further include additional apparatus configured to protect the electrical signals, the subsystem(s) 14, and/or interface circuitry thereof, from, for example, the magnetic resonance RF pulses generated by the MRI system. For example, one or more of filtering or other techniques for attenuating RF pulses, clamp or limiter circuits, and bandpass filtering with rapid recoveries to brief disturbances may be employed within the pathway 100 in a similar manner to that described above with respect to the electrical pathway 82 of the high-impedance channel 78 to add a further measure of protection for the electrical signals, the subsystem(s) 14, and/or interface circuitry thereof.

In addition to the high- and low-impedance channels 78, 80 described above for electrically coupling the catheter 12, and the high- and low-impedance electrical pathways 46, 48 thereof, in particular, to the subsystem(s) 14 of the EP lab system 10, in an exemplary embodiment the interface module 26 may further comprise one or more low-impedance channels 110 having one or more electrical pathways for electrically coupling one or more patch electrodes, such as, for example, those described above with respect to the visualization, navigation, and/or mapping system 16 and the ablation system 22, with one or more corresponding subsystems 14. For purposes of clarity and illustration, the description below will be limited to an embodiment wherein the interface module 26 comprises a single low-impedance channel 110. It will be appreciated, however, that in other exemplary embodiments, the interface module 26 may comprise any number of low-impedance channels, and therefore, embodiments wherein the interface module 26 comprises two or more low-impedance channels configured to electrically couple one or more patch electrodes with one or more corresponding subsystems 14 remain within the spirit and scope of the present disclosure.

Figure 6:
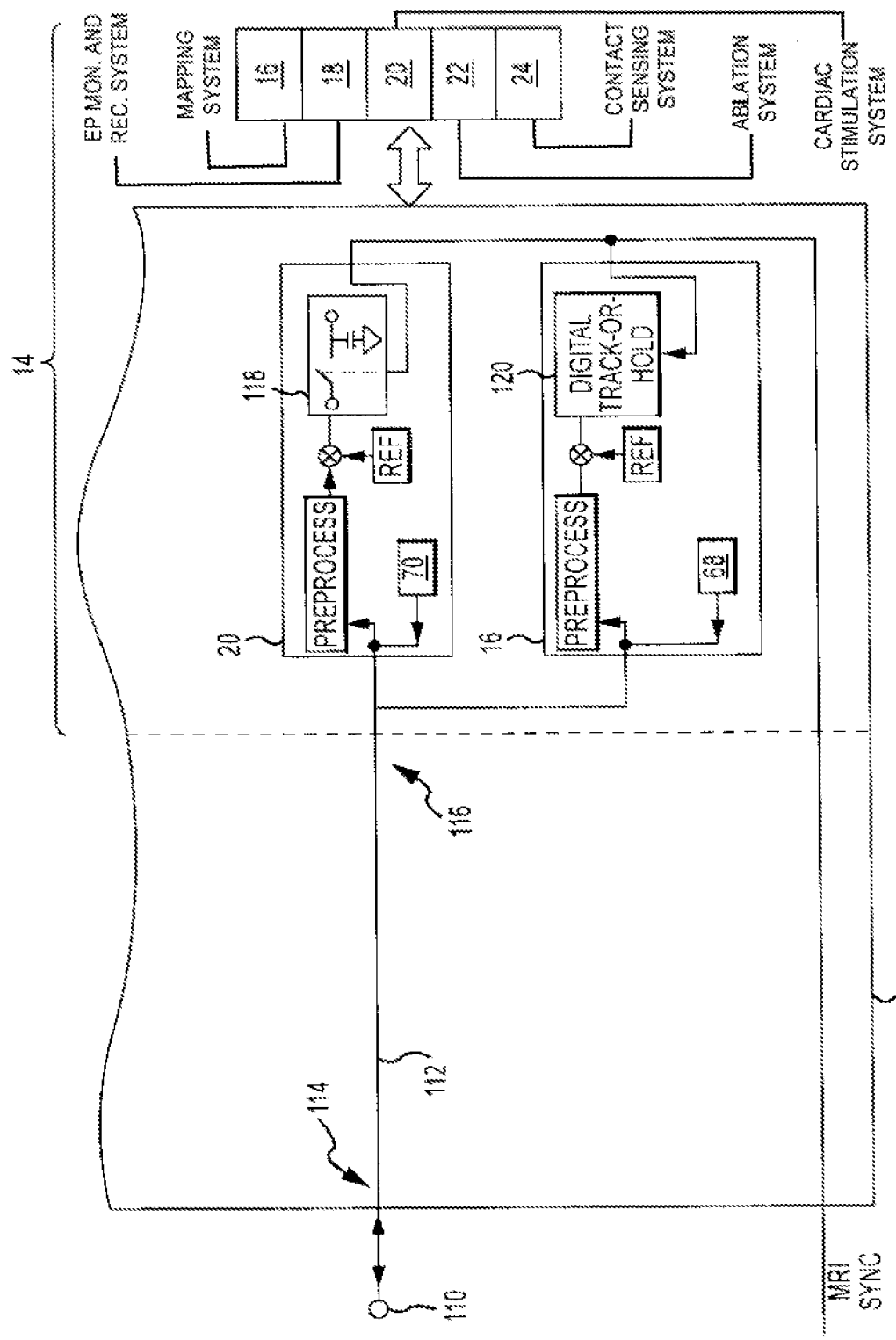
FIG. 6 is a diagrammatic and schematic view of a portion of another exemplary interface module of the EP lab system illustrated in FIG. 1.

With reference to FIG. 6, the low-impedance channel 110 comprises an electrical pathway 112 having a first end 114 and a second end 118. The pathway 112 is configured to provide a direct and uninterrupted pathway between one or more of the subsystem(s) 14 or interface circuitry thereof, and one or more of the patch electrodes corresponding thereto. For example, in an exemplary embodiment, the patch electrodes 60 of the visualization, navigation, and/or mapping system 16 are configured to source current signals used, in part, by the system 16 in determining the position and orientation of one or more catheter mounted electrodes 44. Accordingly, such electrical signals may be transmitted or communicated from the system 16 to the corresponding patch electrode(s) over the electrical pathway 112. In an exemplary embodiment, these patch electrodes 60 may also be utilized to sense voltages resulting from the sourced current signals to provide more steady determinations as to the electrode locations. Accordingly, the electrical signals corresponding to the sensed voltage, for example, may be transmitted or communicated from the patch electrode(s) to the system 16 over the electrical pathway 112.

Similarly, in an exemplary embodiment, the patch electrodes 60 may be configured to source excitation signals and sense response signals that are used, in part, by the tissue contact sensing system 20 in determining the degree of contact between an electrode 44 and the tissue 28 (not shown). Accordingly, source excitation signals may be transmitted or communicated from the system 20 to the corresponding patch electrode(s) over the electrical pathway 112, and the sensed response signals may be transmitted or communicated from the patch electrode(s) to the system 20 over the electrical pathway 112. Thus, in such an embodiment, the first end 114 of the electrical pathway 112 is configured to be electrically coupled to one or more of the patch electrodes 60, and the second end 116 of the electrical pathway 112 is configured to be electrically coupled to one or more subsystem(s) 14 or components or interface circuitry thereof.

Due to the nature of some of the electrical signals sensed or generated by the patch electrodes, to provide protection to those signals communicated or transmitted over the electrical pathway 112, as well as to the circuitry of the corresponding subsystem(s) 14 or interface circuitry thereof, from the various magnetic resonance components or artifacts described above, either the subsystem(s) 14 or certain components or interface circuitry thereof may include a means to invoke a blanking function or other temporal mechanisms configured to suppress artifacts caused by the magnetic resonance gradient field and/or RF pulses. In an exemplary embodiment, an interrupter circuit 118 electrically coupled between the electrical pathway 112 and the subsystem(s) 14 or interface circuitry thereof may be employed.

For example, in the exemplary embodiment illustrated in FIG. 6 wherein one or more patch electrodes transmit or communicate sensed electrical signals to the tissue contact sensing system 20, the system 20, or certain components or interface circuitry thereof, comprises an interrupter circuit 118. As with the interrupter circuits described elsewhere herein, the interrupter circuit 118 may comprise, for example, a track-or-hold circuit comprising a switched capacitor, and is configured to disconnect the system 20 and/or certain components or interface circuitry thereof from the electrical pathway 112. Due to the nature of the signals transmitted or communicated to the system 20, in an exemplary embodiment, the interrupter circuit 118 is implemented at a point or location in the electronics or circuitry of the system 20 that is after that which processes the electrical signals to resolve the complex impedance into its component parts. Accordingly, in such an embodiment, the interrupter circuit 118 may be electrically coupled to the output side of the impedance sensor 72 of the system 20.

In an embodiment, the interrupter circuit 118 may receive a signal to synchronize the sensing functions of the subsystem(s) 14 with the magnetic resonance sequence of the MRI system. For example, in an exemplary embodiment, the interrupter circuit 118 may receive as an input a "sync" signal generated by the MRI system to synchronize the sensing functions of the subsystem(s) 14 with the magnetic resonance sequence of the MRI system.

More particularly, when there are no magnetic resonance gradient field pulses (and possibly magnetic resonance RF pulses), the sync signal causes a switch of the circuit to close and the sensing or tracking function of the electrical signals proceeds normally. In such an instance, the capacitor of the circuit may provide a certain degree of low pass filtering. However, in response to magnetic resonance gradient field pulses (and possibly magnetic resonance RF pulses), the sync signal causes the switch to open to disconnect the system 20 from the electrical pathway 112 and the sensed or tracked electrical signal (or the most recent values of the complex impedance components) is/are effectively held by the capacitor until the switch is once again closed. As a result, the sensing function of the system 20 operates largely unchanged.

While the description above is with respect to an embodiment wherein the sync signal is generated by the MRI system, it will be appreciated that the present disclosure is not meant to be so limited. Rather, in other exemplary embodiments, the sync signal may be generated by a sync signal generator comprising circuitry or components other than the MRI system. For instance, the system 10 (e.g., the interface module 26 or one or more subsystems 14 thereof) may comprise an analog circuit, such as, for example, a differentiator configured to monitor the rate of change on an electrical pathway, such as, for example, an electrical pathway of one of the high- or low-impedance channels 78, 80, 110. In such an embodiment, when the rate of change exceeds a certain predetermined threshold value, the circuit may produce a sync signal that may be used as described above.

In another embodiment, the system 10 (e.g., the interface module 26 or one or more subsystems 14 thereof) may comprise an analog comparator configured to monitor the voltage level on an electrical pathway, such as, for example, an electrical pathway of one of the high- or low-impedance channels 78, 80, 110 and to produce a sync signal when the voltage exceeds a certain predetermined threshold value. As with the embodiment described immediately above, the sync signal may be used in the same manner described above.

In yet another embodiment, the system 10 (e.g., the interface module 26 or one or more subsystems 14 thereof) may comprise a dedicated analog sensor (e.g., a magnetic field sensor) configured to detect when the gradient field pulses and/or the magnetic resonance RF pulses are applied by the MRI system, and to generate a sync signal when such pulses are detected. The generated sync signal may be used in the same manner described above.

In yet still another exemplary embodiment, a software or firmware component configured to monitor the digitized signal and to initiate specific action when the amplitude or rate of change of the signal exceeds a certain predetermined value may be used. Accordingly, it will be appreciated by those having ordinary skill in the art that the sync signal may be generated in any number of ways, each of which remains within the spirit and scope of the present disclosure.

As further illustrated in FIG. 6, in an exemplary embodiment wherein one or more patch electrodes transmit or communicate sensed electrical signals to the visualization, navigation, and/or mapping system 16, the system 16 may also comprise a means by which the system 16 may be interrupted or disconnected from the electrical pathway 112. In this instance, however, rather than having an interrupter circuit like that described above (i.e., interrupter circuit 118), the system 16 may comprise a digital track-or-hold 120 that is configured to achieve the same result as the interrupter circuit 118 described above. In an exemplary embodiment, the track-or-hold 120 is implemented at a point or location within the electronics or circuitry of the system 16 that is after that which processes the electrical signals to determine electrode positions so as to hold the most recent digital representation of electrode position in response to magnetic resonance gradient field pulses.

Accordingly, the electrical pathway 112 may provide a path over which electrical signals may be transmitted or communicated between one or more subsystems 14 and one or more patch electrodes corresponding thereto. As such, embodiments wherein the pathway 112 is configured to allow for the transmission and/or receipt of electrical signals from or by one or more subsystems 14 remain within the spirit and scope of the present disclosure.

In an exemplary embodiment, the interface module 26 further comprises a housing within which the electrical pathways of the high- and low-impedance channels described above are housed. In such an embodiment, the housing may include a plurality of electrical ports or connectors configured to electrically couple the high- and low-impedance channels thereof with high- and low-impedance electrical pathways 46, 48 of the catheter 12, patch electrodes, and the subsystem(s) or corresponding components or interface circuitry thereof. More particularly, the electrical ports or connectors are configured to be mated with complementary connectors of the high- and low-impedance electrical pathways 46, 48, patch electrodes, and cables/wires connecting the interface module 26 to the subsystems 14 or components/interface circuitry thereof. As briefly described above, in an exemplary embodiment, the housing may be further configured to house certain portions or components of one or more of the subsystem(s) 14, or signal processing/interface circuitry thereof. For example, signal sources of one or more subsystem(s), amplifiers, signal conditioning or preprocessing circuitry, and/or interrupter circuits may be disposed within the housing of the interface module 26. Alternatively, some or all of these components or circuitry corresponding to one or more of the subsystem(s) 14 may be separate and distinct from, but electrically coupled to the interface module 26.

Although only certain embodiments have been described above with a certain degree of particularity, those skilled in the art could make numerous alterations to the disclosed embodiments without departing from the scope of this disclosure. Joinder references (e.g., attached, coupled, connected, and the like) are to be construed broadly and may include intermediate members between a connection of elements and relative movement between elements. As such, joinder references do not necessarily infer that two elements are directly connected/coupled and in fixed relation to each other. Additionally, the terms "electrically connected" and "electrically coupled" are meant to be synonymous with each other, and, along with the phrase "in communication" are meant to be construed broadly to encompass both wired and wireless connections and communications. It is intended that all matter contained in the above description or shown in the accompanying drawings shall be interpreted as illustrative only and not limiting. Changes in detail or structure may be made without departing from the scope of the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An interface module for an electrophysiology laboratory (EP lab) system configured for use with a magnetic resonance imaging (MRI) system, the EP lab system including a medical device and at least one subsystem, the at least one subsystem including a diagnostic subsystem or a therapeutic subsystem, the interface module comprising:
 a housing;
 a first port on an exterior of the housing, the first port configured to mate with a first connector of the medical device that is electrically coupled to a high-impedance pathway of the medical device;
 a second port on the exterior of the housing, the second port configured to mate with a second connector of the medical device that is electrically coupled to a low-impedance pathway of the medical device;
 a third port on the exterior of the housing, the third port configured to mate with a first connector of the at least one subsystem;
 a fourth port on the exterior of the housing, the fourth port configured to mate with a second connector of the at least one subsystem;
 a high-impedance channel located within the housing, the high-impedance channel comprising first wired circuitry extending between the first port and the third port within the housing, the first wired circuitry configured to attenuate magnetic resonance radio frequency pulses and gradient field pulses generated by the MRI system while still communicating first electrical signals between the medical device and the at least one subsystem; and
 a low-impedance channel located within the housing and including a plurality of electrical pathways, each of the plurality of electrical pathways comprising second wired circuitry extending between the second port and the fourth port within the housing, the second wired circuitry configured to communicate second electrical signals between the medical device and the at least one subsystem.

2. The interface module of claim 1, wherein the first wired circuitry comprises a high input impedance amplifier.

3. The interface module of claim 1, wherein the low-impedance channel is a first low-impedance channel, and the interface module further includes a second low-impedance channel configured to electrically couple a patch electrode with the at least one subsystem.

4. The interface module of claim 1, wherein the first wired circuitry comprises a low-pass filter configured to be electrically coupled to the high-impedance electrical pathway of the medical device and to attenuate the magnetic resonance radio frequency pulses generated by the MRI system.

5. The interface module of claim 4, wherein the first wired circuitry further comprises a voltage limiter circuit electrically coupled to an output of the low-pass filter and configured to attenuate the magnetic resonance gradient field pulses generated by the MRI system.

6. The interface module of claim 5, wherein the first wired circuitry further comprises a high input impedance amplifier configured to be electrically coupled between an output of the voltage limiter circuit and the at least one subsystem to which the high-impedance electrical pathway of the medical device is coupled.

7. The interface module of claim 1, wherein:
 one electrical pathway of the plurality of electrical pathways of the low-impedance channel is configured to provide an uninterruptable connection between the low-impedance electrical pathway of the medical device and the at least one subsystem to which the low-impedance electrical pathway of the medical device is coupled; and
 another electrical pathway of the plurality of electrical pathways comprises an interrupter circuit, the interrupter circuit configured to be electrically coupled between the low-impedance electrical pathway of the medical device and the at least one subsystem to which the low-impedance electrical pathway of the medical device is coupled.

8. A system comprising:

the interface module of claim 1; and the medical device comprising the first connector of the medical device, the second connector of the medical device, the high-impedance pathway of the medical device that is electrically coupled to the first connector of the medical device, and the low-impedance pathway of the medical device that is electrically coupled to the second connector of the medical device.

9. The system of claim 8, wherein the high-impedance electrical pathway has an impedance of greater than or equal to 2kΩ.

10. The system of claim 8, wherein the high-impedance electrical pathway includes a non-ferromagnetic electrical conductor having a high impedance.

11. The system of claim 10, wherein the electrical conductor is constructed of a metal alloy selected from the group consisting of:

a nickel-chromium alloy, a nickel-iron alloy, a copper-nickel alloy, and a manganese-nickel-copper alloy.

12. The system of claim 8, wherein the high-impedance electrical pathway includes an electrical conductor with a plurality of segments and a resistor element electrically connected in series between a pair of conductor segments.

13. The system of claim 8, wherein the low-impedance electrical pathway includes an inductive element configured to:

attenuate magnetic resonance radio frequency pulses, and limit a magnitude of radio frequency currents induced in the low-impedance electrical pathway.

14. The system of claim 13, wherein the inductive element is a choke.

15. The system of claim 13, wherein the low-impedance electrical pathway further includes a non-ferromagnetic electrical conductor having a plurality of segments, and the inductive element is electrically connected in series between a pair of conductor segments.

16. The system of claim 8, further comprising a temperature sensor electrically coupled to the low-impedance electrical pathway.

17. The interface module of claim 1, wherein the first ends of each of the plurality of electrical pathways are electrically coupled to one another.

18. The system of claim 8, wherein the high-impedance electrical pathway is configured to limit a magnitude of radio frequency currents induced in the high-impedance pathway by magnetic resonance radio frequency pulses.

19. The interface module of claim 7, wherein the interrupter circuit comprises a sample-and-hold circuit.

20. The interface module of claim 19, wherein the sample-and-hold circuit comprises a capacitor configured to disconnect the subsystem.

* * * * *